(12) United States Patent
Harris et al.

(10) Patent No.: US 11,304,634 B2
(45) Date of Patent: Apr. 19, 2022

(54) NON-INVASIVE BLOOD GLUCOSE SENSOR

(71) Applicant: Basil Leaf Technologies, LLC, Paoli, PA (US)

(72) Inventors: Basil M. Harris, Paoli, PA (US);
George C. Harris, Ramsey, NJ (US);
Edward L. Hepler, Malvern, PA (US)

(73) Assignee: Basil Leaf Technologies, LLC, Paoli, PA (US)

( * ) Notice: Subject to any disclaimer, the term of this patent is extended or adjusted under 35 U.S.C. 154(b) by 360 days.

(21) Appl. No.: 16/347,077

(22) PCT Filed: Nov. 3, 2017

(86) PCT No.: PCT/US2017/059869
§ 371 (c)(1),
(2) Date: May 2, 2019

(87) PCT Pub. No.: WO2018/085625
PCT Pub. Date: May 11, 2018

(65) Prior Publication Data
US 2020/0060585 A1     Feb. 27, 2020

Related U.S. Application Data

(60) Provisional application No. 62/573,087, filed on Oct. 16, 2017, provisional application No. 62/544,845, (Continued)

(51) Int. Cl.
*A61B 5/1455*     (2006.01)
*A61B 5/145*     (2006.01)
*A61B 5/00*     (2006.01)

(52) U.S. Cl.
CPC ........ *A61B 5/14532* (2013.01); *A61B 5/1455* (2013.01); *A61B 5/6806* (2013.01); *A61B 2562/0238* (2013.01); *A61B 2562/164* (2013.01)

(58) Field of Classification Search
CPC ... A61B 5/145; A61B 5/1455; A61B 5/14551; A61B 5/14552; A61B 5/14532;
(Continued)

(56) References Cited

U.S. PATENT DOCUMENTS 4,825,879 A     5/1989 Tan
5,054,487 A *  10/1991 Clarke ................ A61B 5/1455
                                                          600/316

(Continued)

FOREIGN PATENT DOCUMENTS

WO     2016027202     2/2016
WO     2016051016     4/2016
(Continued)

OTHER PUBLICATIONS

Dantu Vishnu et al: "Non-invasive blood glucose monitor based on spectroscopy using a smartphone," 2014 36th annual international conference of the IEEE engineering in medicine and biology society, Aug. 26, 2014, pp. 3695-3698, XP032674779.
(Continued)

*Primary Examiner* — Chu Chuan Liu
(74) *Attorney, Agent, or Firm* — Fisherbroyles, LLP

(57) ABSTRACT

A non-invasive blood sensor includes a body configured to mate with a tissue surface; a blue light source disposed on the sensor body; and a photodetector disposed on the sensor body at a suitable position for capturing light emanating from the tissue surface after emission from the blue light source, e.g., by one of: transmission, reflection, and transflection. The sensor bodies may further include a green, a red and/or an infrared light source. The light source(s) and photodetector(s) may be supported on a support structure configured to register with a corresponding portion of human anatomy in a predetermined fashion, and support the light sources and photodetectors in a defined spatial rela-
(Continued)

tionship. The sensor or an integrated meter may include a controller programmed to receive signals from the photodetector and calculate blood glucose value as function of the signals received from the photodetector after emission by the light source(s).

14 Claims, 17 Drawing Sheets

Related U.S. Application Data filed on Aug. 13, 2017, provisional application No. 62/432,035, filed on Dec. 9, 2016, provisional application No. 62/417,226, filed on Nov. 3, 2016.

(58) Field of Classification Search
CPC ... A61B 5/6806; A61B 5/6824; A61B 5/6829; A61B 5/6826; A61B 2562/164; A61B 2562/0238

See application file for complete search history.

(56) References Cited

U.S. PATENT DOCUMENTS

| | | | |
|---|---|---|---|
| 5,203,329 A * | 4/1993 | Takatani | A61B 5/14552 356/41 |
| 5,830,137 A | 11/1998 | Scharf | |
| 6,763,256 B2 | 7/2004 | Kimball | |
| 8,554,297 B2 | 10/2013 | Moon | |
| 8,818,476 B2 | 8/2014 | Besko | |
| 8,971,978 B2 | 3/2015 | Ho | |
| 9,314,197 B2 | 4/2016 | Eisen | |
| 2006/0224058 A1 | 10/2006 | Mannheimer | |
| 2007/0244377 A1 | 10/2007 | Cozad | |
| 2012/0277559 A1 | 11/2012 | Kohl-Bareis | |
| 2015/0245773 A1 | 9/2015 | Lamego | |
| 2016/0192867 A1 | 7/2016 | Esenaliev | |
| 2017/0209081 A1 * | 7/2017 | Davidson | A61B 5/1455 |
| 2017/0281081 A1 * | 10/2017 | Nousiainen | A61B 5/02427 |

FOREIGN PATENT DOCUMENTS

| | | |
|---|---|---|
| WO | 2017060746 | 4/2017 |
| WO | 2017087051 | 5/2017 |

OTHER PUBLICATIONS

Extended European Search Report dated Jul. 3, 2020 in European Application No. 17867264.8.
Abdallah et al., "Design of a Compact Multi-Sensor System for Non-Invasive Glucose Monitoring Using Optical Spectroscopy," International Conference on Electronics, Biomedical Engineering and its Applications (ICEBEA 2012) Jan. 7-8, 2012.
Facchinetti et al., "Signal Processing Algorithms Implementing the 'Smart Sensor' Concept to Improve Continuous Glucose Monitoring in Diabetes," Journal of Diabetes Science and Technology, vol. 7, Issue 5, pp. 1308-1318, Sep. 2013.
International Preliminary Report on Patentability for International Application No. PCT/US2017/059869, dated May 7, 2019.
International Search Report for International Application No. PCT/US2017/059869, dated Jan. 4, 2018.
Khan et al., "System Design for Organic Pulse Oximeter," IEEE, 2015, pp. 83-86.
OSRAM Opto Semicondutors, Light is wearable Health Monitoring and Fitness Tracking, retrieved from www.osram-os.com in Oct. 2017.
Written Opinion of the International Searching Authority for International Application No. PCT/US2017/059869, dated Jan. 4, 2018.

* cited by examiner

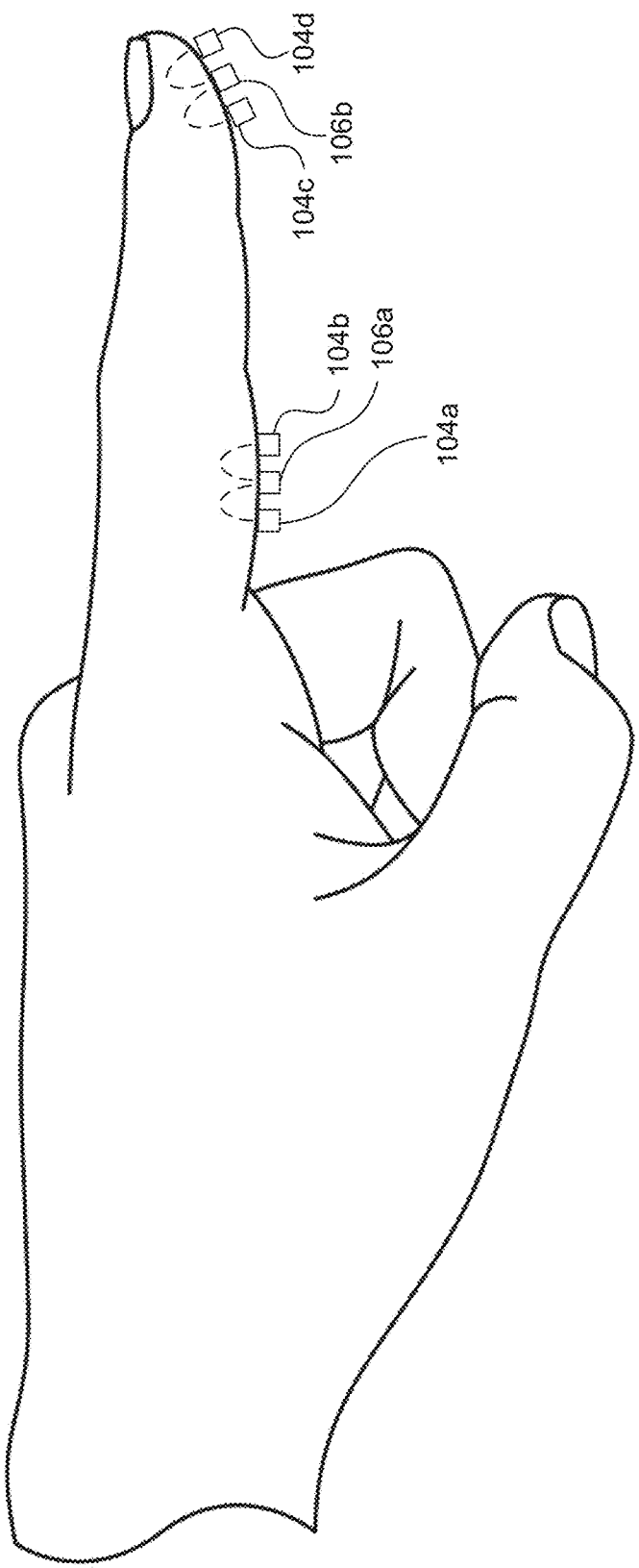

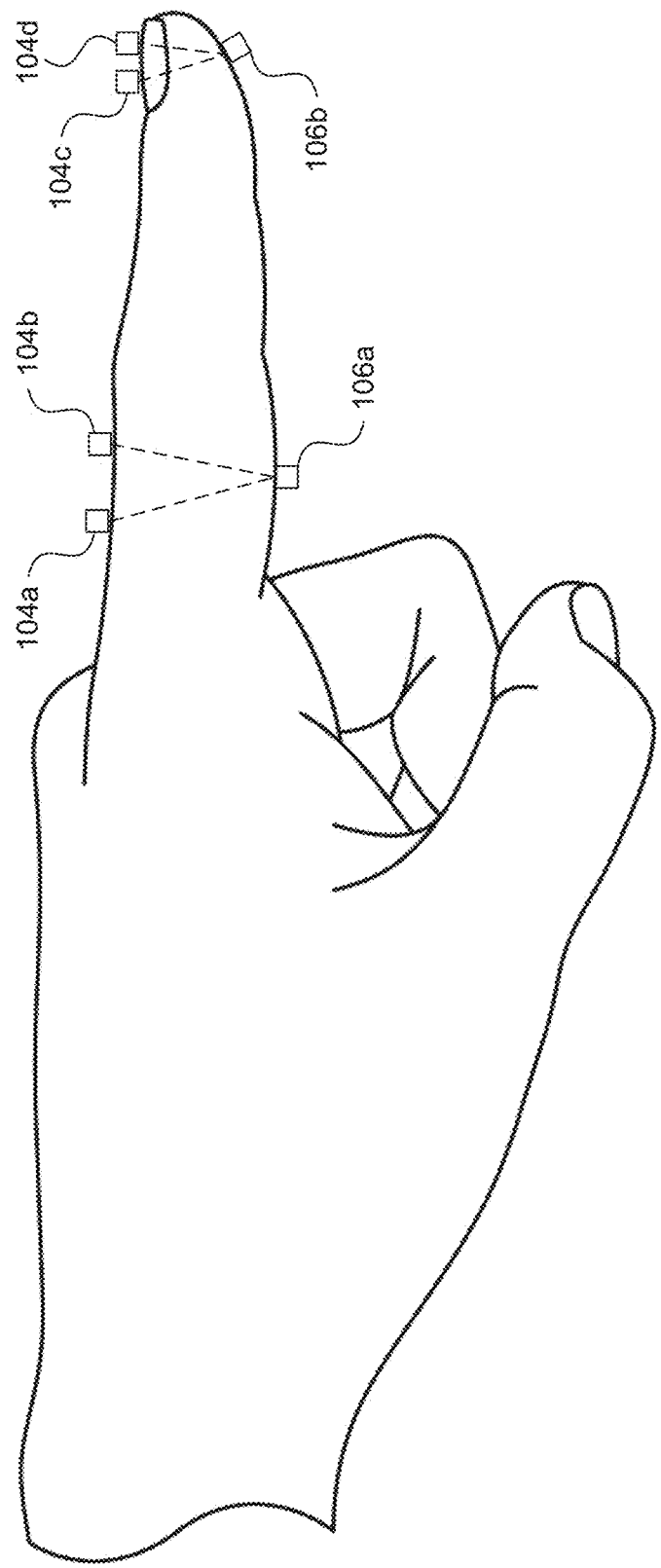

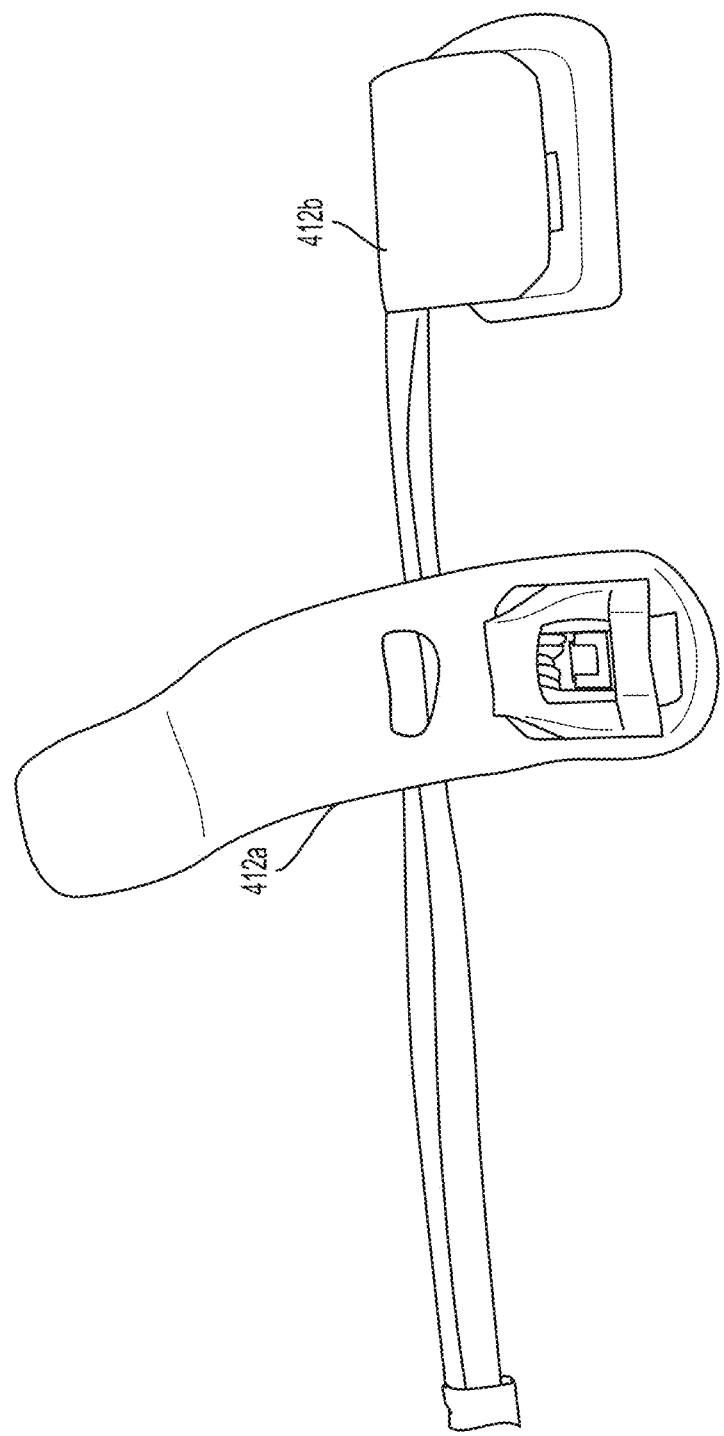

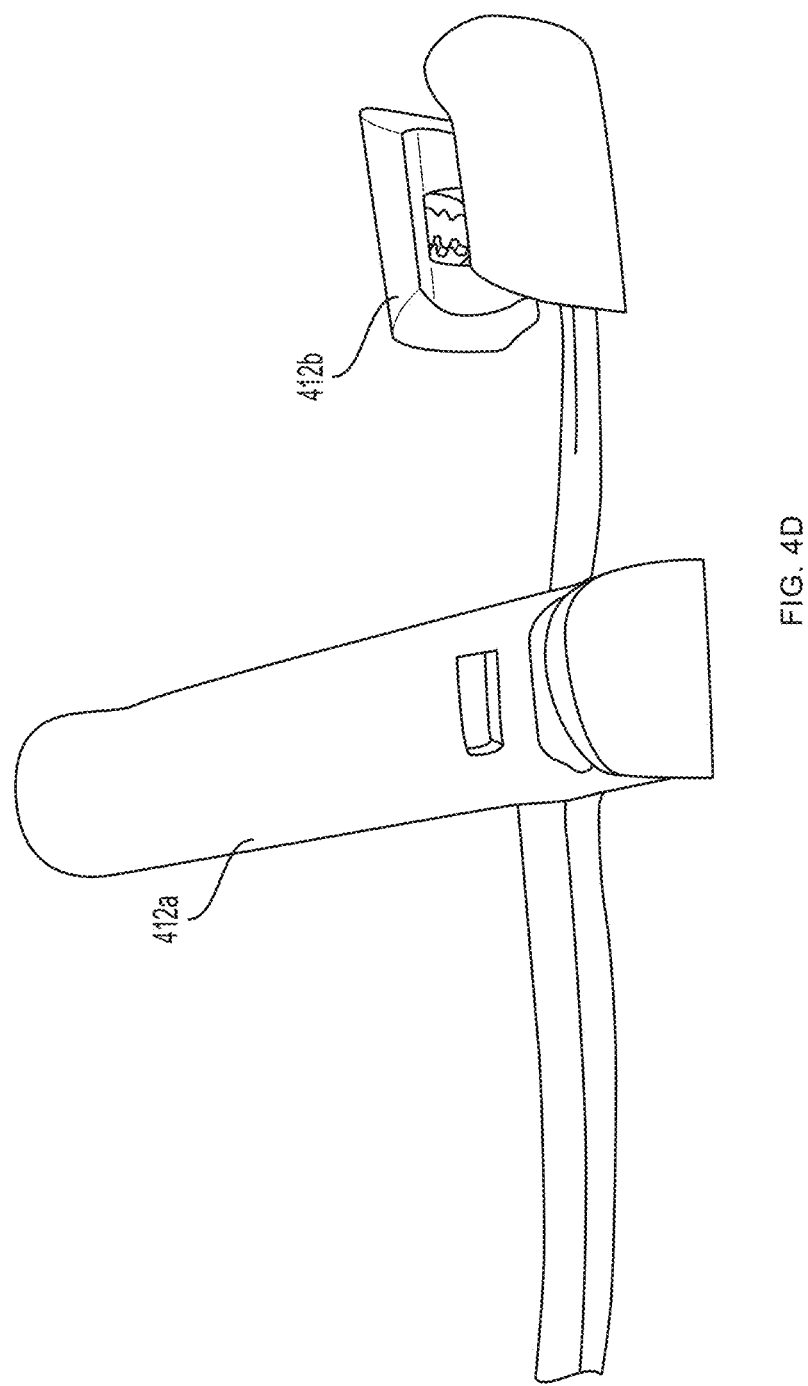

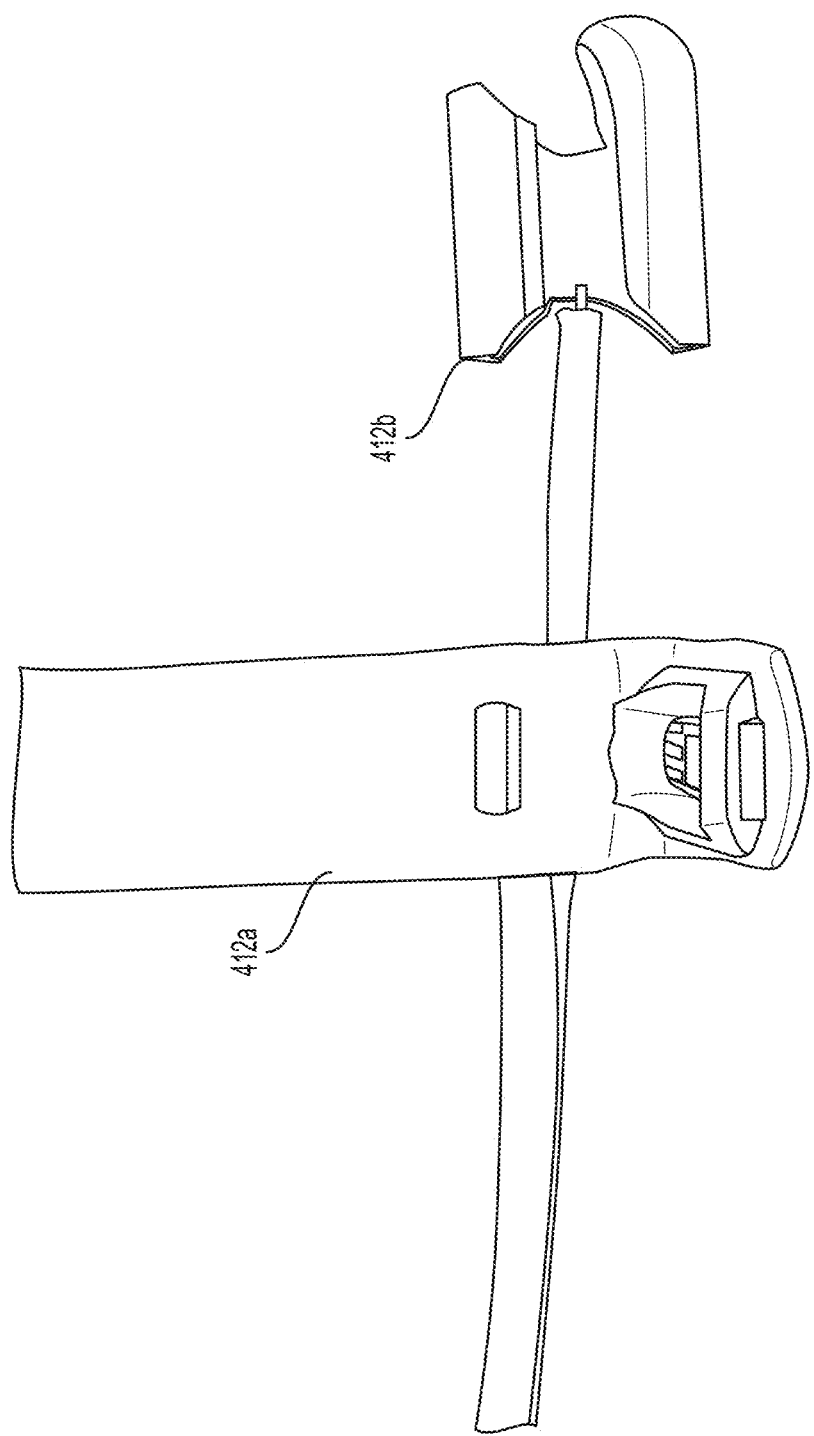

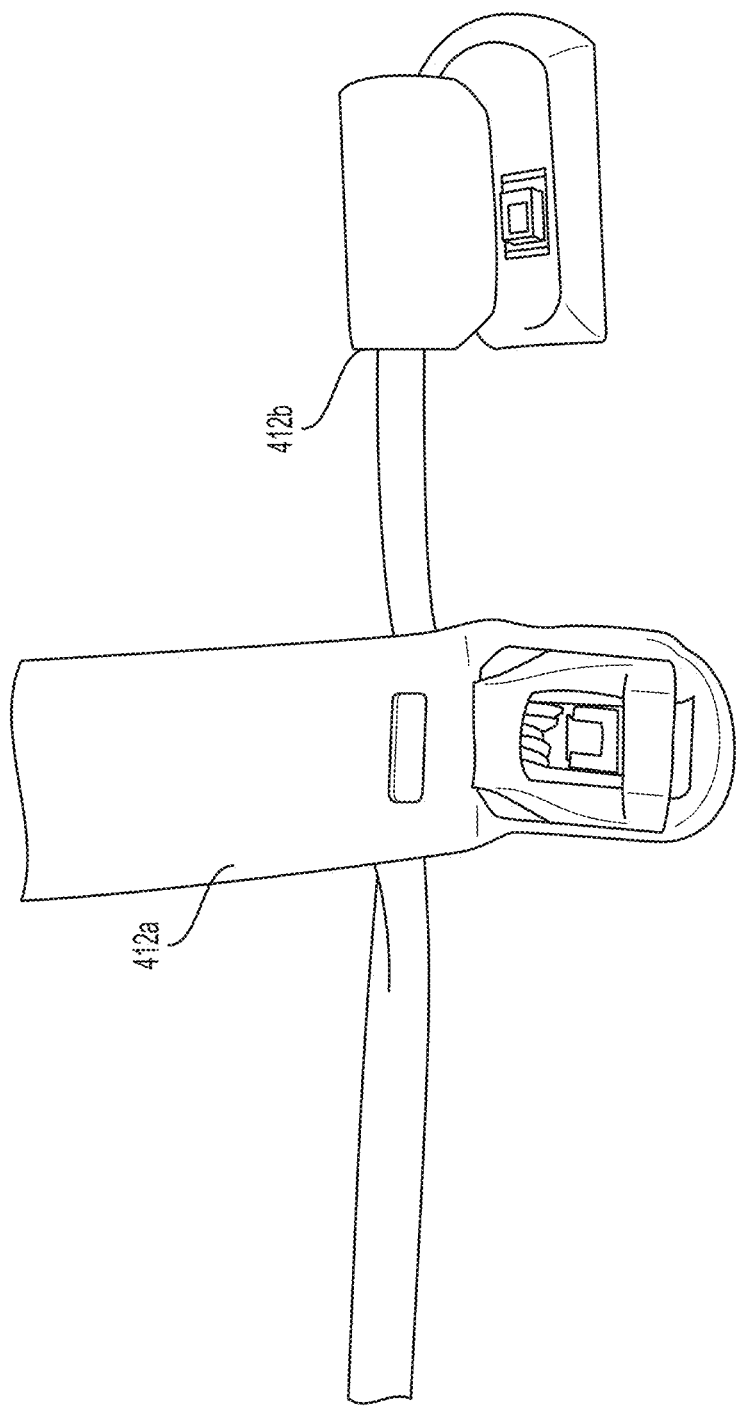

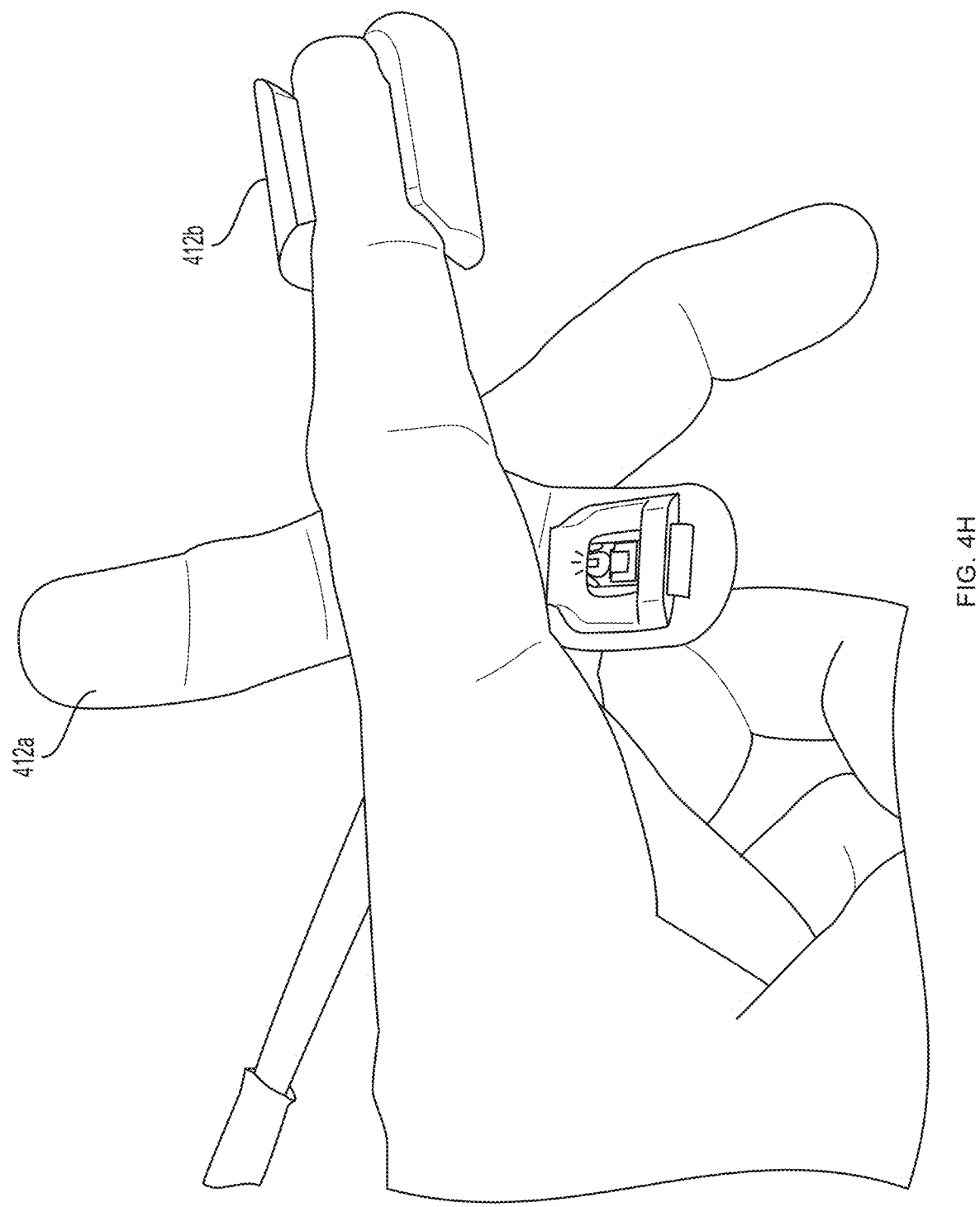

NON-INVASIVE BLOOD GLUCOSE SENSOR

CROSS-REFERENCE TO RELATED APPLICATIONS

This application is a national stage application of International Application No. PCT/US2017/059869, filed Nov. 3, 2017, which claims the benefit of priority of U.S. Provisional Patent Application Nos. 62/417,226, filed Nov. 3, 2016, 62/432,035, filed Dec. 9, 2016, 62/544,845, filed Aug. 13, 2017, and 62/573,087, filed Oct. 16, 2017, the entire disclosures of all of which are hereby incorporated herein by reference.

FIELD OF THE INVENTION

The present invention relates generally to and more particularly to blood glucose measuring devices, and more particularly, to sensors and methods for measuring blood glucose in the body without the need for a blood sample.

BACKGROUND OF THE INVENTION

Despite the prevalence of diabetes, there remains a need for an accurate non-invasive device for measuring blood glucose levels. For example, common approaches to monitoring blood glucose levels are invasive due to the need to puncture the skin and obtain a blood sample. This is painful and creates a risk of infection, among other challenges.

SUMMARY

A non-invasive blood sensor includes a body configured to mate with a tissue surface; a blue light source disposed on the sensor body; and a photodetector disposed on the sensor body at a suitable position for capturing light emanating from the tissue surface after emission from the blue light source, e.g., by one of: transmission, reflection, and transflection. The sensor bodies may further include a green, a red and/or an infrared light source. The light source(s) and photodetector(s) may be supported on a support structure configured to register with a corresponding portion of human anatomy in a predetermined fashion, and support the light sources and photodetectors in a defined spatial relationship. The sensor or an integrated meter may include a controller programmed to receive signals from the photodetector and calculate blood glucose value as function of the signals received from the photodetector after emission by the light source(s).

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

FIGS. 1B and 1C depict an exemplary positioning of light sources and photodetectors along a subject's finger for measurement of reflectance/transflectance and transmission, respectively, according to embodiments of the invention.

FIG. 4B-4J depicts portions of the blood glucose sensor of FIG. 4A.

DEFINITIONS

Figure 1A:
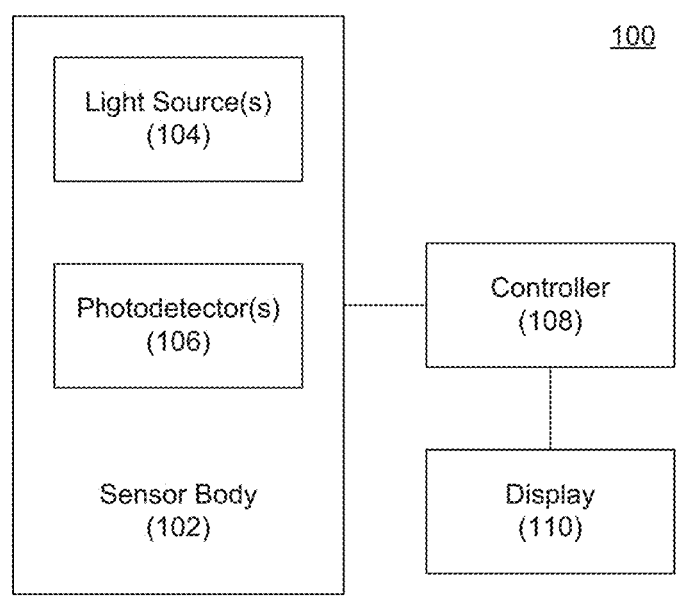
FIG. 1A is a block diagram of a non-invasive blood glucose sensor according to an embodiment of the invention.

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION

Aspects of the invention provide non-invasive blood glucose sensors. Without being bound by theory, Applicant believes that different components of blood are characterized by different absorption spectra such that the application of multiple wavelengths of light will yield different transmission, reflectance, and/or transflectance spectra depending on the content of the subject's blood (e.g., the level of blood glucose within the blood) that can act as "signatures" usable for analyzing the components of blood.

Pulse oximetry exploits a difference in absorption of red and infrared light between oxygenated and deoxygenated blood to calculate a saturation of peripheral oxygen ($SpO_2$). However, the absorption of red and infrared wavelengths is not substantially impacted by blood glucose levels to permit detection of blood glucose levels solely from red and infrared absorption. That is, the absorption of red and infrared light is substantially the same regardless of whether a subject's blood glucose levels are high, low, or in between. However, as discussed herein, blood glucose levels can be measured using blue light, green light, or combinations thereof.

Applicant has discovered that blood glucose levels reliably influence the absorption of certain wavelengths of light, particularly in the blue and/or green spectra. Embodiments of the invention provide devices, methods, and computer-readable media that measure absorption at appropriate wavelengths and calculate blood glucose levels based on that absorption.

Referring to FIG. 1A, one embodiment of the invention provides a non-invasive blood glucose meter 100 including a sensor body 102, one or more light sources 104, and one or more photodetectors 106. As discussed further herein and without being bound by theory, Applicant believes that blue and/or green light absorption is a relatively strong predictor of blood glucose levels. Accordingly, embodiments of the invention can utilize only blue and/or green light sources 104. Other embodiments can add additional light sources 104 (e.g., red and/or infrared light sources), which can further improve the accuracy of a detected blood glucose value and/or enable detection of other values of interest.

Light Sources

Light sources 104 can be light-emitting diodes (LEDs), fiber optics, or any other device capable of generating and/or transmitting a desired wavelength to a tissue (e.g., skin) surface. Suitable LEDs are available from a variety of manufacturers and are detailed in the Appendix to this application.

Exemplary wavelength ranges and peak wavelengths are provided in Table 1 below.

TABLE 1

Exemplary Light Source Wavelengths

| Abbreviation | Color | Exemplary Wavelength Range | Exemplary Peak Wavelength | Exemplary Peak Wavelength Range |
|---|---|---|---|---|
| B | Blue | 380-495 nm | 465 nm | 454-476 nm |
| G | Green | 495-590 nm | 515 nm | 497-533 nm |
| R | Red | 590-750 nm | 660 nm | 650-670 nm |
| IR | Infrared | 750-1000 nm | 940 nm | 915-965 nm |

In one embodiment, one or more fiber optics function as the one or more light sources by multiplexing and/or transmitting light from at least one LED or other light source located remote from the tissue surface.

In another embodiment, a broadband or white light source 104 can be filtered at the light source 104 to emit one or more wavelengths of interest. The filtering can change to emit a plurality of wavelengths in sequence or in parallel.

Photodetectors

Photodetector(s) 106 can be a photodiode such as a silicon photodiode (e.g., Product No. PDB-C171SM available from Luna Optoelectronics of Roanoke, Va.), a phototransistor, and the like.

Photodetector(s) 106 detect light after partial absorption of light emitted by one of the light sources 104 and convert the light into electrical current. For example, at least a portion of the emitted light may be absorbed by various components of blood within tissue of the subject such that the amplitude of the detected light is less than from the amplitude of the emitted light.

Positioning of Light Sources and Photodetectors

In view of the prevalence of capillaries carrying blood skin or tissue surfaces, embodiments of the invention can be applied to most, if not all, tissue surfaces of a body without the need to position the sensor 100 over a particular blood vessel. However, particular embodiments can be configured for application to particular regions such as a finger, toe, forehead, head, ear, earlobe, chest, wrist, ankle, nostril, and the like.

Figure 1D:
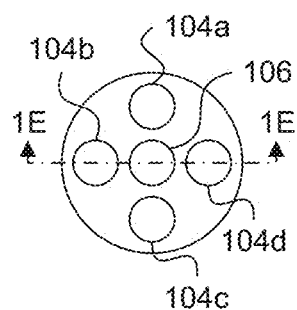
FIGS. 1D and 1E depict an exemplary light source and photodetector sensor assembly according to an embodiment of the invention.
Figure 1E:
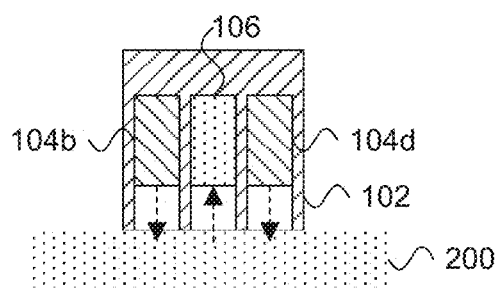
Figure 3:
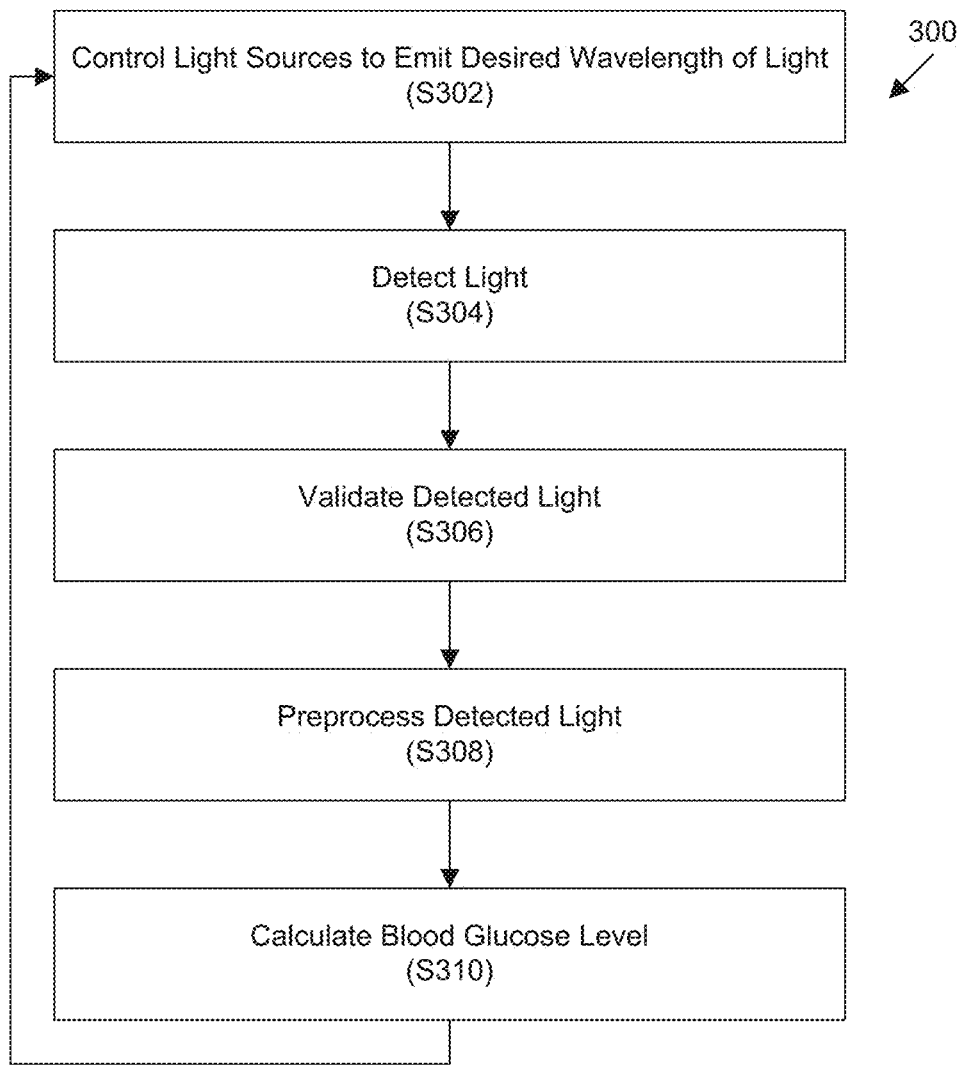
FIG. 3 depicts a method of controlling a non-invasive blood glucose sensor according to an embodiment of the invention.

The light source(s) 104 and the photodetector(s) 106 can be positioned along the tissue surface so that the photodetector(s) 106 detect light emitted by one or more light sources 104 after absorption of some of the emitted light by blood within the tissue. As illustrated in U.S. Pat. Nos. 6,763,256, 8,818,476, and 9,314,197, photodetector(s) 106 can be located on the same surface as the light sources 104 to detect reflectance and/or transflectance of emitted light through the tissue (as also depicted in FIG. 1B) and/or the opposite side (e.g., perpendicularly opposite) of the tissue (e.g., finger) to detect transmission of the light through the tissue (as also depicted in FIG. 1C). In reflectance oximetry, the light sources 104 are typically placed around a central photodetector 106 (e.g., on a single body for abutting a tissue surface), which can be surrounded by a light shield (e.g., an optically opaque sensor body 102) to minimize detection of light that has not traveled through the subject's tissue as depicted in FIGS. 1D and 1E. Such an embodiment having an approximately 8 mm diameter is depicted in FIG. 3.11 of John T B Moyle, *Pulse Oximetry* 31 (2d ed. 2002).

Sensor Housings

Referring still to FIGS. 1D and 1E, the sensor body 102 can be a wand or probe that can be placed or held over a desired tissue surface.

This assembly can be further mounted to, coupled to, and/or incorporated within a support structure component for securing the assembly against a tissue surface. Exemplary components include a strap adapted to wrap around a body part (e.g., an about 6 cm to about 10 cm strap to accommodate placement over a finger, an about 15 cm to about 23 cm strap to accommodate placement around a wrist, and the like) that can be secured to itself after wrapping around a tissue, a sleeve, a glove, and the like. The strap, sleeve, glove, cuff, spring-loaded case or clip, or other component can include one or more elastic members, hook-and-loop fasteners (e.g., those available under the VEL-CRO® trademark from Velcro Industries B.V. of the Netherlands Antilles), and the like.

In each case, the sensor body 102 can be designed to abut and/or register or mate with the intended anatomical structure and further support the light source(s) 104 and photodetector(s) 106 in a defined spatial relationship so that they will be properly positioned during use, according to the reflectance, transmittance, or transflectance mode of operation for which the sensor 100 is designed.

Sensor body 102 can be configured for application to one or more specific tissue surfaces. For example, sensor body 102 can be configured for application to a subject's finger and/or fingertip such as depicted in FIGS. 1B and 1C and disclosed in U.S. Pat. Nos. 4,825,879, 8,554,297, 8,818,476, and 9,314,197 and U.S. Patent Application Publication Nos. 2006/0224058 and 2007/0244377, on a wrist as disclosed in U.S. Pat. No. 9,314,197, in a contact lens as disclosed in U.S. Pat. No. 8,971,978, on a heel (e.g., an infant's heel), and the like. For example, non-invasive blood glucose sensor 100 can be, or can be incorporated within, a watch and/or an activity tracker (e.g., devices sold under the APPLE WATCH® trademark by Apple, Inc. of Cupertino, Calif., the FITBIT® trademark by Fitbit, Inc. of San Francisco, Calif., and the like).

In various embodiments, the sensor body 102 shields or substantially shields the light source(s) 104, the photodetector 106, and/or the tissue from ambient light. For example, in FIGS. 1D and 1E, a shell 102 surrounds light sources 104 and/or photodetector 106 such that light is directed (and sometimes collimated) toward tissue 200 and/or such that photodetector 106 can only receive light that emanates from the tissue 200. While four light sources and a single photodetector are shown in FIGS. 1D and 1E, in other embodiments, more or less light sources 104 and/or photodetectors 106 can be implemented. For other, e.g., transmission, implementations, the light sources 104 and photodetector(s) 106 can be spaced on opposite sides of tissue 200 as discussed herein, for example, in a spaced linear array along a flexible wrap.

In one embodiment, the sensor 100 includes a support structure (e.g., a tether, sock, glove or sleeve) having a configuration specifically designed to register with a specific portion of the human anatomy, e.g., a finger, a hand, a forearm, etc., and one or more sensor bodies are arranged on the support structure in one or more predetermined locations corresponding to the intended locations on the human anatomy, e.g., by mounting them on or to a substrate such as a flexible glove or flexible sleeve. The support structure thereby acts somewhat like a three-dimensional template or jig for arranging the sensor(s) on the human anatomy in a desired spatial arrangement. An exemplary embodiment of such a support structure is shown in FIGS. 4A-4J. FIGS. 4K-4L illustrate exemplary embodiments of support structures designed to register with specific portions of human anatomy according to an embodiment of the present invention. In this manner, the sensor's structure assists the user in using the sensor properly, as it does not require the user to follow extensive directions, anatomical knowledge or medical expertise for proper sensor placement relative to anatomical structures, but rather simplifies the process in a manner suitable for a layperson—e.g., requiring merely placing one's hand in a glove, or one's foot in a sock.

In other embodiments, the sensor may include a support structure that is more generic, and capable of registering with distinctly different parts of the human anatomy, such a spring-loaded clip or clamp.

As described further below, FIGS. 4A-4J depict an embodiment of a meter capable of measuring not only blood glucose but also other vital signs. Embodiments of the invention are not limited to finger-worn devices.

Control of Non-Invasive Blood Glucose Sensor

Figure 2:
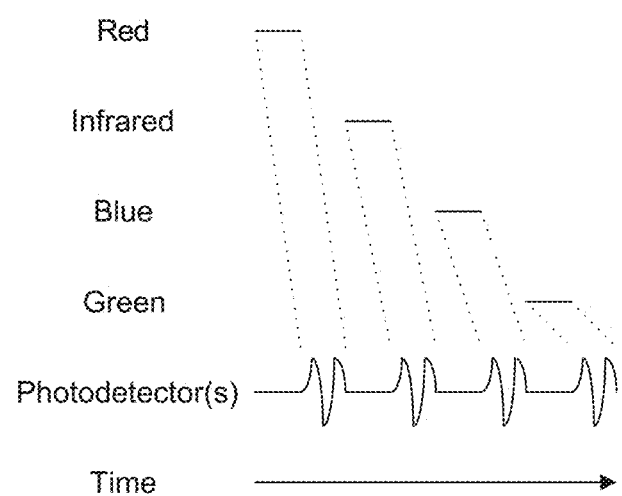
FIG. 2 depicts the association of photodetector signals with a previously or concurrently applied color according to an embodiment of the invention.

In various embodiments, each light source of one or more light sources 102 can be activated at different times such that only one light source 102 is activated at a time. For example, as depicted in FIG. 2, the resulting light received by photodetector(s) 106 can be associated with a particular light source 104 (and color) based on a time delay between activation of a particular light source 104 and later detection by the photodetector(s) 106.

Referring now to FIG. 3, a method 300 of controlling a non-invasive blood glucose sensor is provided. While specific steps in a predetermined order are illustrated in FIG. 3, in various embodiments, one or more of the steps may be excluded and/or additional steps can be added. Further, the steps may be performed in any order.

In step S302, a light source is controlled to emit a first light signal. In various embodiments, this can include controlling the light source to emit a light signal at a specific wavelength of light. In one embodiment, each of the light sources can be controlled to serially apply each light signal at a specific wavelength (e.g., blue, then green, then red, then infrared, although any order can be used). The light sources can be applied at non-overlapping periods of time. In various embodiments, the light sources can be turned on and off at such a frequency (e.g., 60 Hz or greater) that the light sources may appear to be continuously illuminated to the human eye.

In step S304, a resulting light can be detected by the one or more photodetectors. A controller can be programmed to monitor and record detected light based on the sequence of emission on step S302. For example, light can be first detected in the blue wavelength, then green, then red, then infrared. A waveform is observed wherein the peaks correspond to the pulsatile blood flow during systole and the trough is the resting phase of diastole. The difference between the peak and the trough is the measured amplitude of interest.

In step S306, the resulting light signal can be validated based on expected ranges of values (e.g., to confirm that the light sources and photodetector(s) are properly positioned). For example, the resulting light signals can be assessed to ensure that each exhibits a pulsatile waveform of the type expected from blood flow within a subject. In various embodiments, validation is performed each time a measurement is performed. In other embodiments, validation is performed after the meter has been applied to a subject and, once the device has been validated, validation is no longer performed. In yet other embodiments, validation is performed based upon subject-supplied commands or when the measured blood glucose levels deviate from an expected range.

In step S308, the resulting light signal can be preprocessed (e.g., by averaging and/or other statistical techniques over several heartbeats, data points, or period of time) to remove or minimize noise, outliers, or other variations. For example, a last-in, first-out (LIFO) queue of n data points (e.g., on the order of 10, 100, and the like) can be maintained for statistical processing.

Various techniques for validating and preprocessing data in the pulse oximetry field as well as hardware for implementing the same are described in John T B Moyle, *Pulse Oximetry* (2d ed. 2002) and can be applied prior to calculating of a blood glucose level.

In step S310, the subject's blood glucose level can be calculated as described below.

The method can then be repeated continuously or periodically to provide updated blood glucose levels.

Calculation of Blood Glucose Level

Embodiments of the invention can calculate blood glucose levels based on the amplitudes received from the one or more photodetector(s) 106 in response to the application of one or more frequencies of light. The amplitudes can be normalized with regards to the base of the waveform (i.e., the ambient or dark signal) for one or more frequencies of light.

The equations described herein and equivalent equations act to isolate the effect of blood glucose level on absorption of particular colors from the effects of other absorbents along the optical path.

Equation (1) below provides one exemplary equation for calculating a blood glucose level using a device such as depicted in FIGS. 4A-4J using blue light measurements.

$$\text{glucose} = (\alpha)(B) + \frac{(\delta)^B}{(\varepsilon)} + (\zeta) \qquad (1)$$

Equation (2) below provides one exemplary equation for calculating a blood glucose level using a device such as depicted in FIGS. 4A-4J using green light measurements.

$$\text{glucose} = (\alpha)(G) + \frac{(\delta)^G}{(\varepsilon)} + (\zeta) \qquad (2)$$

Equation (3) below provides one exemplary equation for calculating a blood glucose level using a device such as depicted in FIGS. 4A-4J using blue and green light measurements.

$$\text{glucose} = (\alpha)\left(\frac{B}{G}\right) + \frac{(\delta)^{\frac{B}{G}}}{(\varepsilon)} + (\zeta) \qquad (3)$$

Equation (4) below provides one exemplary equation for calculating a blood glucose level using a device such as depicted in FIGS. 4A-4J using blue, green, red, and infrared light measurements.

$$\text{glucose} = (\alpha)\left(\frac{B+G}{R}\right) + (\beta)\ln\left((\gamma)\frac{B+G}{IR}\right) + (\delta)\ln\left((\varepsilon)\frac{G}{B}\right) + (\zeta) \qquad (4)$$

Exemplary calibration values for Equations (1)-(4) are provided in Table 2 below.

TABLE 2

| Calibration Values | |
|---|---|
| α | 150 |
| β | 0.5 |
| γ | 0.5 |
| δ | 3.0 |
| ε | 2.0 |
| ζ | −25 |

Equation (5) below provides another exemplary equation for calculating a blood glucose level using a device such as depicted in FIGS. 4A-4J using blue, green, red, and infrared light measurements.

$$\text{Glucose Factor} = \frac{\alpha - B\ln\frac{B}{\beta} - G\ln\frac{B}{\gamma} - \varepsilon\ln\frac{B}{\delta} - B\ln\frac{G}{\zeta} - G\ln\frac{G}{\eta} - \iota\ln\frac{G}{\theta} + \kappa\frac{B+G+R+IR}{B+G}}{\lambda} \qquad (5)$$

Exemplary calibration values for Equation (5) are provided in Table 3 below.

TABLE 3

| Calibration Values | | | |
|---|---|---|---|
| α | 100,000 | η | 2,500 |
| β | 1,500 | θ | 2,500 |
| γ | 1,500 | ι | 5,000 |
| δ | 1,500 | κ | 200 |
| ε | 3,000 | λ | 25,000 |
| ζ | 2,500 | | |

A glucose level can be determined using the Glucose Factor calculated using Equation (5) and a calibration equation. One example of a calibration equation is:

$$\text{Device Calculated Glucose Level} = 53.961 \, e^{0.4006(\text{Glucose Factor})} \qquad (6)$$

Although exemplary calibration values are provided for the Equations herein, a person of ordinary skill in the art will appreciate that these calibration values may vary for a particular implementation (e.g., using light source(s) 104 of varying spectra and/or intensity, photodetector(s) 106 of varying spectra and/or sensitivity, contemplated placement of sensor 100, and the like). Particular calibration values for a given embodiment, including those embodiments using Equations (1)-(4), can be determined by obtaining amplitude values for a plurality of wavelengths and blood glucose levels obtained by other methods for a test population of subjects. Various fitting algorithms can be used to optimize the calibration values to minimize errors in prediction as will be appreciated by those skilled in the art. Exemplary algorithms are described in treatises such as Rudolf J. Freund et al., *Regression Analysis* (2d ed. 2006); P. G. Guest, *Numerical Methods of Curve Fitting* (1961); and Harvey Motulsky & Arthur Christopoulos, *Fitting Models to Biological Data Using Linear and Nonlinear Regression* (2003).

Additionally or alternatively, calibrations can be performed on a subject-level. For example, one or more ground-truth blood glucose values can be obtained, e.g., through queries to the user (e.g., through a user interface) or from one or more sources such as the user's electronic medical record, a computer application or service (e.g., software/services available under the APPLE® HEALTHKIT™ trademark by Apple, Inc. of Cupertino, Calif., the GOOGLE FIT® trademark by Google Inc. of Mountain View, Calif., and the like). For example, a user can enter one or more blood glucose levels obtained using a personal (home) glucose meter that can be associated with a particular date and time. Those levels can be used as a ground truth and associated with light intensity measurements from the same date and time. This allows for calibration to a particular subject and deviations from the ground-truth blood glucose level to be measured using light intensity.

Likewise, other functions can be utilized to calculate blood glucose levels based on light absorption. Such functions can use any or all of the terms:

$$\frac{R+B}{B}, \frac{IR+B}{B}, \frac{R+IR+B}{B}, \frac{R+G}{G}, \frac{IR+G}{G}, \frac{R+IR+G}{G},$$

$$\frac{R+B+G}{B}, \frac{IR+B+G}{B}, \frac{R+IR+B+G}{B}, \frac{R+B+G}{G},$$

$$\frac{IR+B+G}{G}, \text{ and } \frac{R+IR+B+G}{G}.$$

Any or all of these terms can be modified by a logarithm to any base, modified by a natural logarithm, raised by e or any other power, arithmetically combined in any way, modified by one or more calibration factors, or otherwise modified algebraically.

Multi-Band Implementations

Some embodiments of the invention utilize multiple bands within each nominal color (e.g., blue, green, red, infrared, and the like). For example, two bands can be measured for each color according to Table 4 below.

TABLE 4

Exemplary Light Source Wavelengths

| Color | Abbreviation | Exemplary Peak Wavelength | Exemplary Peak Wavelength Range |
|---|---|---|---|
| Blue | $B_1$ | 400 nm | 380-430 nm |
| | $B_2$ | 450 nm | 430-495 nm |
| Green | $G_1$ | 500 nm | 495-545 nm |
| | $G_2$ | 550 nm | 545-590 nm |
| Red | $R_1$ | 600 nm | 590-660 nm |
| | $R_2$ | 700 nm | 650-750 nm |
| Infrared | $IR_1$ | 800 nm | 570-850 nm |
| | $IR_2$ | 900 nm | 850-1,000 nm |

In some embodiments, all eight light sources are provided at the same location (e.g., at fingertip). The fingertip is particularly advantageous for all implementations because its anatomy is fairly constant across subjects of various ages and sizes.

Equation (6) below provides exemplary equation for calculating a blood glucose level using two blue, two green, two red, and two infrared light measurements.

$$\text{Glucose Factor} = \frac{\alpha + (\text{Table 5}) + \kappa_{65}\dfrac{B_1 + G_1 + R_1 + IR_1 + B_2 + G_2 + R_2 + IR_2}{B_1 + G_1 + B_2 + G_2}}{\lambda} \quad (6)$$

Combinatorial constituent expressions provided in Table 7 below.

TABLE 5

Combinatorial Expressions $-B_1 \ln \dfrac{B_1}{\beta_1}$ $-B_2 \ln \dfrac{B_2}{\beta_2}$ $-B_2 \ln \dfrac{B_1}{\beta_3}$ $-B_1 \ln \dfrac{B_2}{\beta_4}$ $-G_1 \ln \dfrac{B_1}{\gamma_1}$ $-G_2 \ln \dfrac{B_2}{\gamma_2}$ $-G_2 \ln \dfrac{B_1}{\gamma_3}$ TABLE 5-continued Combinatorial Expressions $-G_1 \ln \dfrac{B_2}{\gamma_4}$ $-\varepsilon_1 \ln \dfrac{B_1}{\delta_1}$ $-\varepsilon_2 \ln \dfrac{B_2}{\delta_2}$ $-B_1 \ln \dfrac{G_1}{\zeta_1}$ $-B_2 \ln \dfrac{G_2}{\zeta_2}$ $-B_2 \ln \dfrac{G_1}{\zeta_3}$ $-B_1 \ln \dfrac{G_2}{\zeta_4}$ $-G_1 \ln \dfrac{G_1}{\eta_1}$ $-G_2 \ln \dfrac{G_2}{\eta_2}$ $-G_2 \ln \dfrac{G_1}{\eta_3}$ $-G_1 \ln \dfrac{G_2}{\eta_4}$ $-\iota_1 \ln \dfrac{G_1}{\theta_1}$ $-\iota_2 \ln \dfrac{G_2}{\theta_2}$ $\kappa_1 \dfrac{B_1 + G_1 + R_1 + IR_1}{B_1 + G_1}$ $\kappa_2 \dfrac{B_1 + G_1 + R_1 + IR_1}{B_1 + G_2}$ $\kappa_3 \dfrac{B_1 + G_1 + R_1 + IR_1}{B_2 + G_1}$ $\kappa_4 \dfrac{B_1 + G_1 + R_1 + IR_1}{B_1 + G_2}$ $\kappa_5 \dfrac{B_1 + G_1 + R_1 + IR_2}{B_1 + G_1}$ $\kappa_6 \dfrac{B_1 + G_1 + R_1 + IR_2}{B_1 + G_2}$ $\kappa_7 \dfrac{B_1 + G_1 + R_1 + IR_2}{B_2 + G_1}$ $\kappa_8 \dfrac{B_1 + G_1 + R_1 + IR_2}{B_1 + G_2}$ $\kappa_9 \dfrac{B_1 + G_1 + R_2 + IR_1}{B_1 + G_1}$

TABLE 5-continued

Combinatorial Expressions $$\kappa_{10} \frac{B_1 + G_1 + R_2 + IR_1}{B_1 + G_2}$$

$$\kappa_{11} \frac{B_1 + G_1 + R_2 + IR_1}{B_2 + G_1}$$

$$\kappa_{12} \frac{B_1 + G_1 + R_2 + IR_1}{B_1 + G_2}$$

$$\kappa_{13} \frac{B_1 + G_2 + R_1 + IR_1}{B_1 + G_1}$$

$$\kappa_{14} \frac{B_1 + G_2 + R_1 + IR_1}{B_1 + G_2}$$

$$\kappa_{15} \frac{B_1 + G_2 + R_1 + IR_1}{B_2 + G_1}$$

$$\kappa_{16} \frac{B_1 + G_2 + R_1 + IR_1}{B_1 + G_2}$$

$$\kappa_{17} \frac{B_2 + G_1 + R_1 + IR_1}{B_1 + G_1}$$

$$\kappa_{18} \frac{B_2 + G_1 + R_1 + IR_1}{B_1 + G_2}$$

$$\kappa_{19} \frac{B_2 + G_1 + R_1 + IR_1}{B_2 + G_1}$$

$$\kappa_{20} \frac{B_2 + G_1 + R_1 + IR_1}{B_1 + G_2}$$

$$\kappa_{21} \frac{B_1 + G_1 + R_2 + IR_2}{B_1 + G_1}$$

$$\kappa_{22} \frac{B_1 + G_1 + R_2 + IR_2}{B_1 + G_2}$$

$$\kappa_{23} \frac{B_1 + G_1 + R_2 + IR_2}{B_2 + G_1}$$

$$\kappa_{24} \frac{B_1 + G_1 + R_2 + IR_2}{B_1 + G_2}$$

$$\kappa_{25} \frac{B_1 + G_2 + R_2 + IR_1}{B_1 + G_1}$$

$$\kappa_{26} \frac{B_1 + G_2 + R_2 + IR_1}{B_1 + G_2}$$

$$\kappa_{27} \frac{B_1 + G_2 + R_2 + IR_1}{B_2 + G_1}$$

$$\kappa_{28} \frac{B_1 + G_2 + R_2 + IR_1}{B_1 + G_2}$$

$$\kappa_{29} \frac{B_1 + G_2 + R_1 + IR_2}{B_1 + G_1}$$

$$\kappa_{30} \frac{B_1 + G_2 + R_1 + IR_2}{B_1 + G_2}$$

$$\kappa_{31} \frac{B_1 + G_2 + R_1 + IR_2}{B_2 + G_1}$$

$$\kappa_{32} \frac{B_1 + G_2 + R_1 + IR_2}{B_1 + G_2}$$

$$\kappa_{33} \frac{B_2 + G_2 + R_1 + IR_1}{B_1 + G_1}$$

$$\kappa_{34} \frac{B_2 + G_2 + R_1 + IR_1}{B_1 + G_2}$$

$$\kappa_{35} \frac{B_2 + G_2 + R_1 + IR_1}{B_2 + G_1}$$

$$\kappa_{36} \frac{B_2 + G_2 + R_1 + IR_1}{B_1 + G_2}$$

$$\kappa_{37} \frac{B_2 + G_1 + R_2 + IR_1}{B_1 + G_1}$$

$$\kappa_{38} \frac{B_2 + G_1 + R_2 + IR_1}{B_1 + G_2}$$

$$\kappa_{39} \frac{B_2 + G_1 + R_2 + IR_1}{B_2 + G_1}$$

$$\kappa_{40} \frac{B_2 + G_1 + R_2 + IR_1}{B_1 + G_2}$$

$$\kappa_{41} \frac{B_2 + G_1 + R_1 + IR_2}{B_1 + G_1}$$

$$\kappa_{42} \frac{B_2 + G_1 + R_1 + IR_2}{B_1 + G_2}$$

$$\kappa_{43} \frac{B_2 + G_1 + R_1 + IR_2}{B_2 + G_1}$$

$$\kappa_{44} \frac{B_2 + G_1 + R_1 + IR_2}{B_1 + G_2}$$

$$\kappa_{45} \frac{B_1 + G_2 + R_2 + IR_2}{B_1 + G_1}$$

$$\kappa_{46} \frac{B_1 + G_2 + R_2 + IR_2}{B_1 + G_2}$$

$$\kappa_{47} \frac{B_1 + G_2 + R_2 + IR_2}{B_2 + G_1}$$

$$\kappa_{48} \frac{B_1 + G_2 + R_2 + IR_2}{B_1 + G_2}$$

$$\kappa_{49} \frac{B_2 + G_1 + R_2 + IR_2}{B_1 + G_1}$$

$$\kappa_{50} \frac{B_2 + G_1 + R_2 + IR_2}{B_1 + G_2}$$

$$\kappa_{51} \frac{B_2 + G_1 + R_2 + IR_2}{B_2 + G_1}$$

$$\kappa_{52} \frac{B_2 + G_1 + R_2 + IR_2}{B_1 + G_2}$$

$$\kappa_{53} \frac{B_2 + G_2 + R_1 + IR_2}{B_1 + G_1}$$

TABLE 5-continued

Combinatorial Expressions $$K_{54} \frac{B_2 + G_2 + R_1 + IR_2}{B_1 + G_2}$$

$$K_{55} \frac{B_2 + G_2 + R_1 + IR_2}{B_2 + G_1}$$

$$K_{56} \frac{B_2 + G_2 + R_1 + IR_2}{B_1 + G_2}$$

$$K_{57} \frac{B_2 + G_2 + R_2 + IR_1}{B_1 + G_1}$$

$$K_{58} \frac{B_2 + G_2 + R_2 + IR_1}{B_1 + G_2}$$

$$K_{59} \frac{B_2 + G_2 + R_2 + IR_1}{B_2 + G_1}$$

$$K_{60} \frac{B_2 + G_2 + R_2 + IR_1}{B_1 + G_2}$$

$$K_{61} \frac{B_2 + G_2 + R_2 + IR_2}{B_1 + G_1}$$

$$K_{62} \frac{B_2 + G_2 + R_2 + IR_2}{B_1 + G_2}$$

$$K_{63} \frac{B_2 + G_2 + R_2 + IR_2}{B_2 + G_1}$$

$$K_{64} \frac{B_2 + G_2 + R_2 + IR_2}{B_1 + G_2}$$

Communication with Other Devices

Embodiments of the non-invasive blood glucose sensor 100 can be designed for repeated use or single use and can use one or more communication links for communicating with a controller 108 as will be further described herein. For example, the non-invasive blood glucose sensor 100 can implement one or more wired or wireless communication protocols.

In one embodiment, the non-invasive blood glucose sensor 100 can include the appropriate hardware and/or software to implement one or more of the following communication protocols: Universal Serial Bus (USB), USB 2.0, IEEE 1394, Peripheral Component Interconnect (PCI), Ethernet, Gigabit Ethernet, and the like. The USB and USB 2.0 standards are described in publications such as Andrew S. Tanenbaum, *Structured Computer Organization Section* § 3.6.4 (5th ed. 2006); and Andrew S. Tanenbaum, *Modern Operating Systems* 32 (2d ed. 2001). The IEEE 1394 standard is described in Andrew S. Tanenbaum, *Modern Operating Systems* 32 (2d ed. 2001). The PCI standard is described in Andrew S. Tanenbaum, *Modern Operating Systems* 31 (2d ed. 2001); Andrew S. Tanenbaum, *Structured Computer Organization* 91, 183-89 (4th ed. 1999). The Ethernet and Gigabit Ethernet standards are discussed in Andrew S. Tanenbaum, *Computer Networks* 17, 65-68, 271-92 (4th ed. 2003).

In other embodiments, the non-invasive blood glucose sensor 100 can include appropriate hardware and/or software to implement one or more of the following communication protocols: BLUETOOTH®, IEEE 802.11, IEEE 802.15.4, and the like. The BLUETOOTH® standard is discussed in Andrew S. Tanenbaum, *Computer Networks* 21, 310-17 (4th ed. 2003). The IEEE 802.11 standard is discussed in Andrew S. Tanenbaum, *Computer Networks* 292-302 (4th ed. 2003). The IEEE 802.15.4 standard is described in Yu-Kai Huang & Ai-Chan Pang, "A Comprehensive Study of Low-Power Operation in IEEE 802.15.4" in *MSWiM'07* 405-08 (2007).

Controller

The non-invasive blood glucose sensor 102 can be sold as a stand-alone peripheral device, or may be sold as part of a sensor including a controller 108 and/or a display device 110, which may all be physically packaged in an integrated meter device.

In one embodiment, the non-invasive blood glucose meter 100 includes a controller 108 configured to obtain resulting signals from the one or more photodetectors 106 of the sensor 102. Controller 108 can be further configured to provide current and/or instructions to each light source 104 to emit light and to each photodetector 106 to measure resulting light intensities.

Controller 108 can be disposed on sensor body 102 or on a substrate separate from sensor body 102. In one embodiment, the controller 108 filters, processes and/or converts the resulting signal or signals to determine a blood glucose value for a subject.

Controller 108 can either be a fixed unit that handles all aspects of control and measurement and outputs a blood glucose level (and potentially other measurements), e.g., through a display or communication with another device, or can rely on an external device (e.g., a smartphone or a computer) including software and/or hardware including instructions for controlling the operation of light source(s) 104 and photodetectors 106 and calculating blood glucose levels based on the received values. For example, controller 108 (or one component thereof) can be worn by the patient (e.g., in a watch, activity tracker, and the like) and control light source(s) 104 and photodetectors 106, but communicate the signals from photodetectors 106 to another component of controller 108 or another device (e.g., a smartphone) for calculation of blood glucose value(s). Collected signals can further be passed from a wearable device to a smartphone and then (e.g., via the internet or other network) to a remote service (e.g., "in the cloud") implementing an blood glucose calculation algorithm.

Controller 108 can be an electronic device programmed to control the operation of the system to achieve a desired result. The controller 108 can be programmed to autonomously determine a blood glucose level in a subject based upon emission and detection of light.

Controller 108 can be a computing device such as a general purpose computer (e.g., a personal computer ("PC"), laptop, desktop), workstation, mainframe computer system, a patient telemetry device, a smartphone (e.g., devices sold under the IPHONE® trademark by Apple, Inc. of Cupertino, Calif., the WINDOWS® trademark by Microsoft Corporation of Redmond Wash., the ANDROID® trademark by Google Inc. of Mountain View, Calif., and the like), a tablet (e.g., devices sold under the IPAD® trademark from Apple Inc. of Cupertino, Calif. and the KINDLE® trademark from Amazon Technologies, LLC of Reno, Nev. and devices that utilize WINDOWS® operating systems available from Microsoft Corporation of Redmond, Wash. or ANDROID® operating systems available from Google Inc. of Mountain View, Calif.), a video game console (e.g., the WII U® console available from Nintendo of America Inc. of Redmond, Wash.; the SONY® PLAYSTATION® console available from Kabushiki Kaisha Sony Corporation of Tokyo, Japan; the MICROSOFT® XBOX® console available from Microsoft Corporation of Redmond, Wash.), smart speaker devices (e.g., devices sold under the HOMEPOD™ trademark by Apple, Inc. of Cupertino, Calif., the AMAZON ECHO™ trademark from Amazon Technologies, LLC of Reno, Nev., the GOOGLE HOME™ trademark by Google Inc. of Mountain View, Calif., and the CASTLEHUB® trademark by CastleOS Software, LLC of Johnston, R. I.), medical devices (e.g., insulin pumps, hospital monitoring systems, intravenous (IV) pumps), electronic medical record (EMR) systems, electronic health record (EHR) systems, and the like.

Controller 108 can be or can include a processor device (or central processing unit "CPU"), a memory device, a storage device, a user interface, a system bus, and/or a communication interface.

A processor can be any type of processing device for carrying out instructions, processing data, and so forth.

A memory device can be any type of memory device including any one or more of random access memory ("RAM"), read-only memory ("ROM"), Flash memory, Electrically Erasable Programmable Read Only Memory ("EEPROM"), and so forth.

A storage device can be any data storage device for reading/writing from/to any removable and/or integrated optical, magnetic, and/or optical-magneto storage medium, and the like (e.g., a hard disk, a compact disc-read-only memory "CD-ROM", CD-ReWritable "CD-RW", Digital Versatile Disc-ROM "DVD-ROM", DVD-RW, and so forth). The storage device can also include a controller/interface for connecting to a system bus. Thus, the memory device and the storage device can be suitable for storing data as well as instructions for programmed processes for execution on a processor.

The user interface can include a touch screen, control panel, keyboard, keypad, display, voice recognition and control unit, or any other type of interface, which can be connected to a system bus through a corresponding input/output device interface/adapter.

The communication interface can be adapted and configured to communicate with any type of external device. The communication interface can further be adapted and configured to communicate with any system or network, such as one or more computing devices on a local area network ("LAN"), wide area network ("WAN"), the internet, and so forth. The communication interface can be connected directly to a system bus or can be connected through a suitable interface.

The controller 108 can, thus, provide for executing processes, by itself and/or in cooperation with one or more additional devices, that can include algorithms for controlling various components of the light source(s) 104 and photodetector(s) 106 in accordance with the present invention. Controller 108 can be programmed or instructed to perform these processes according to any communication protocol and/or programming language on any platform. Thus, the processes can be embodied in data as well as instructions stored in a memory device and/or storage device or received at a user interface and/or communication interface for execution on a processor.

The controller 108 can control the operation of the system components in a variety of ways. For example, controller 108 can modulate the level of electricity provided to a component. Alternatively, the controller 108 can transmit instructions and/or parameters a system component for implementation by the system component.

Implementation in Computer-Readable Media and/or Hardware

The methods described herein can be readily implemented in software that can be stored in computer-readable media for execution by a computer processor. For example, the computer-readable media can be volatile memory (e.g., random access memory and the like), non-volatile memory (e.g., read-only memory, hard disks, floppy disks, magnetic tape, optical discs, paper tape, punch cards, and the like).

Additionally or alternatively, the methods described herein can be implemented in computer hardware such as an application-specific integrated circuit (ASIC).

WORKING EXAMPLES

Working Example 1

Figure 4A:
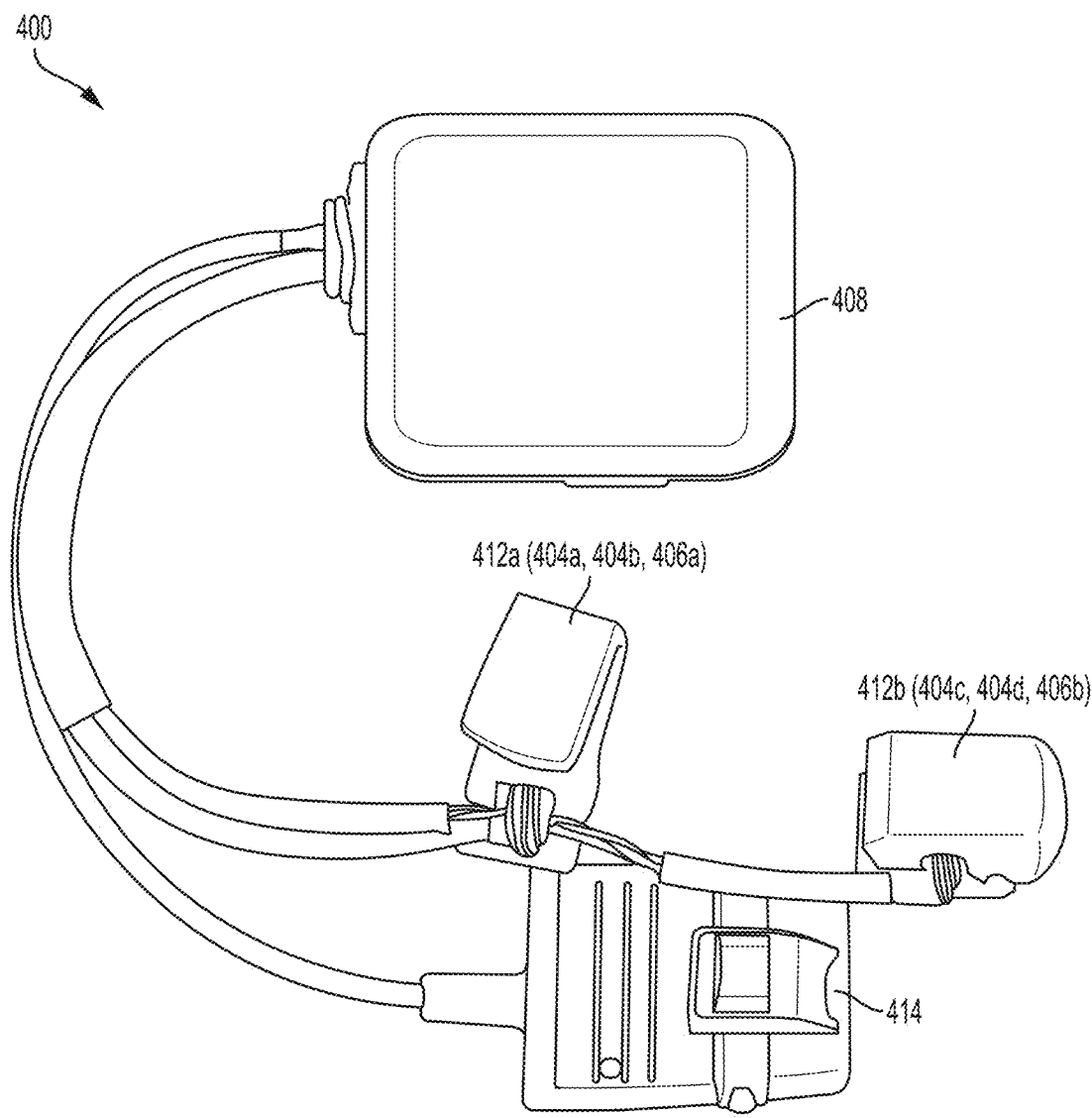
FIG. 4A depicts a non-invasive blood glucose sensor according to an embodiment of the invention.
Figure 4B:
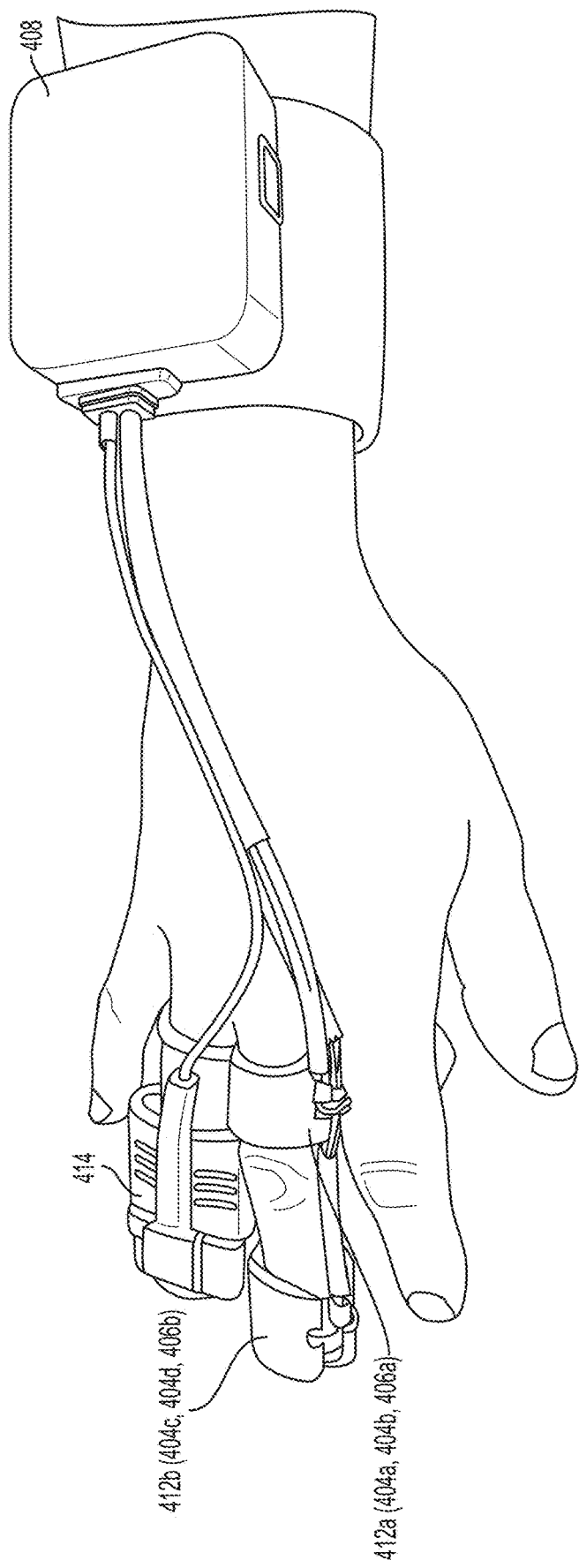
Figure 4G:
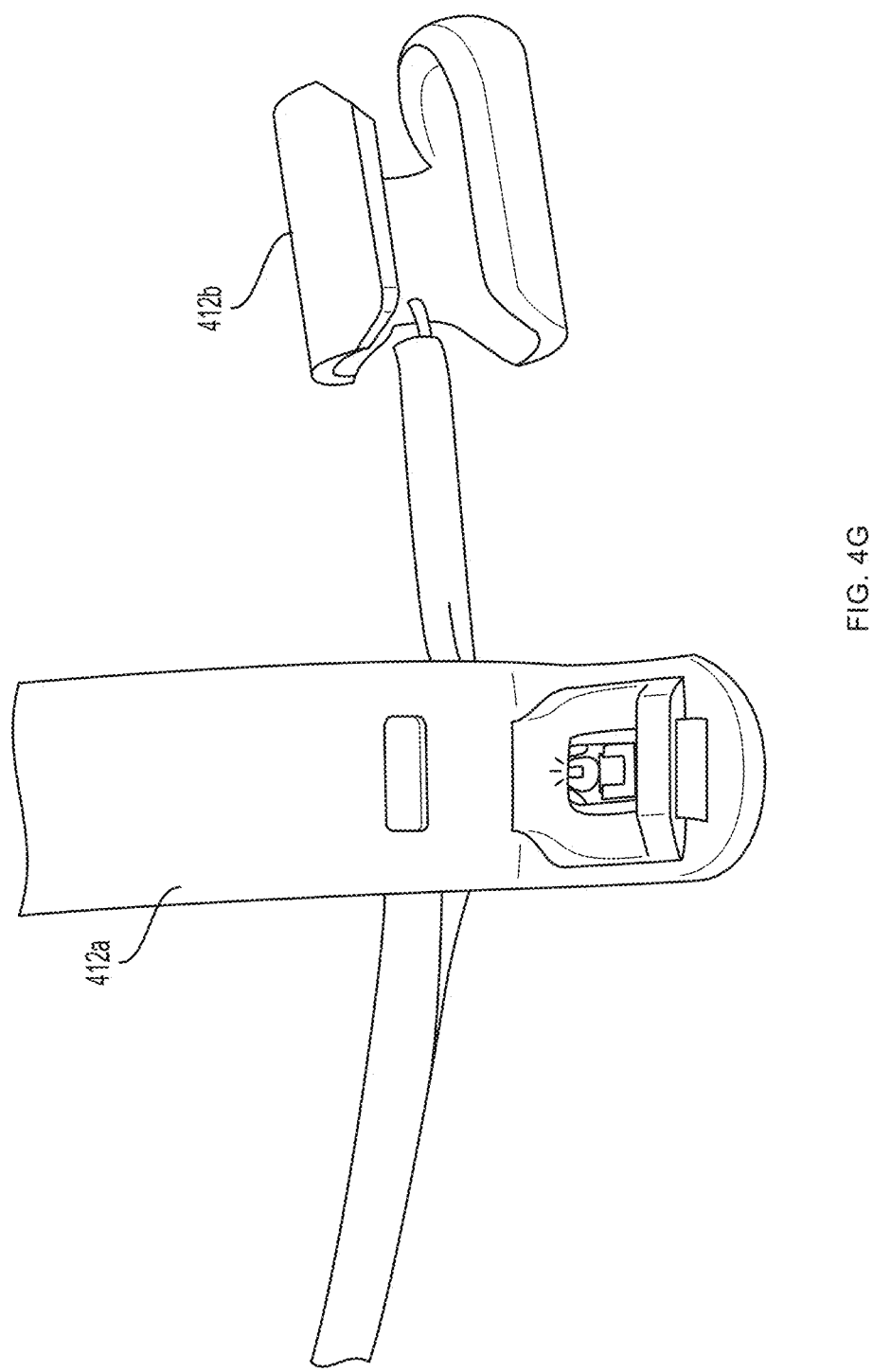
Figure 41:
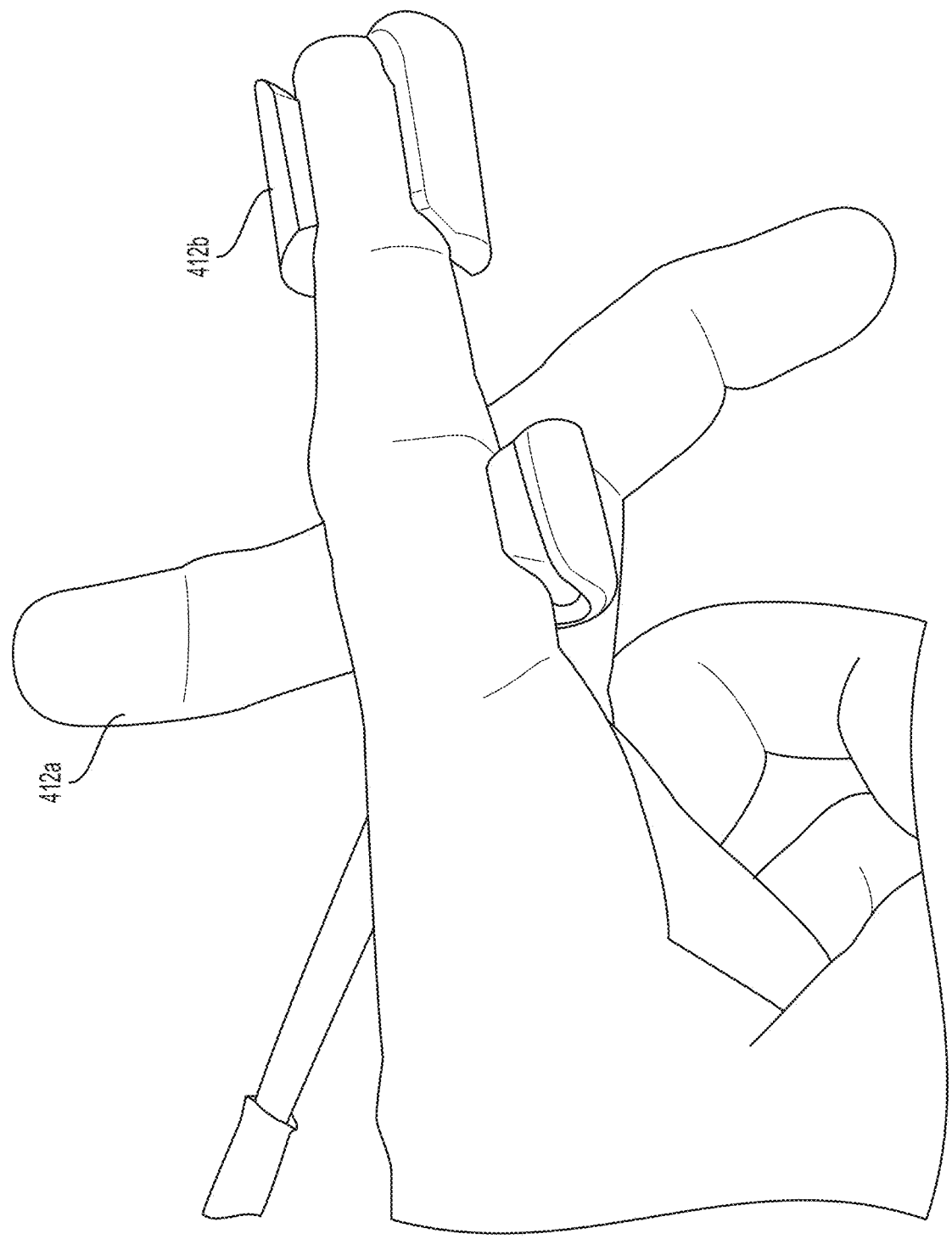
Figure 4J:
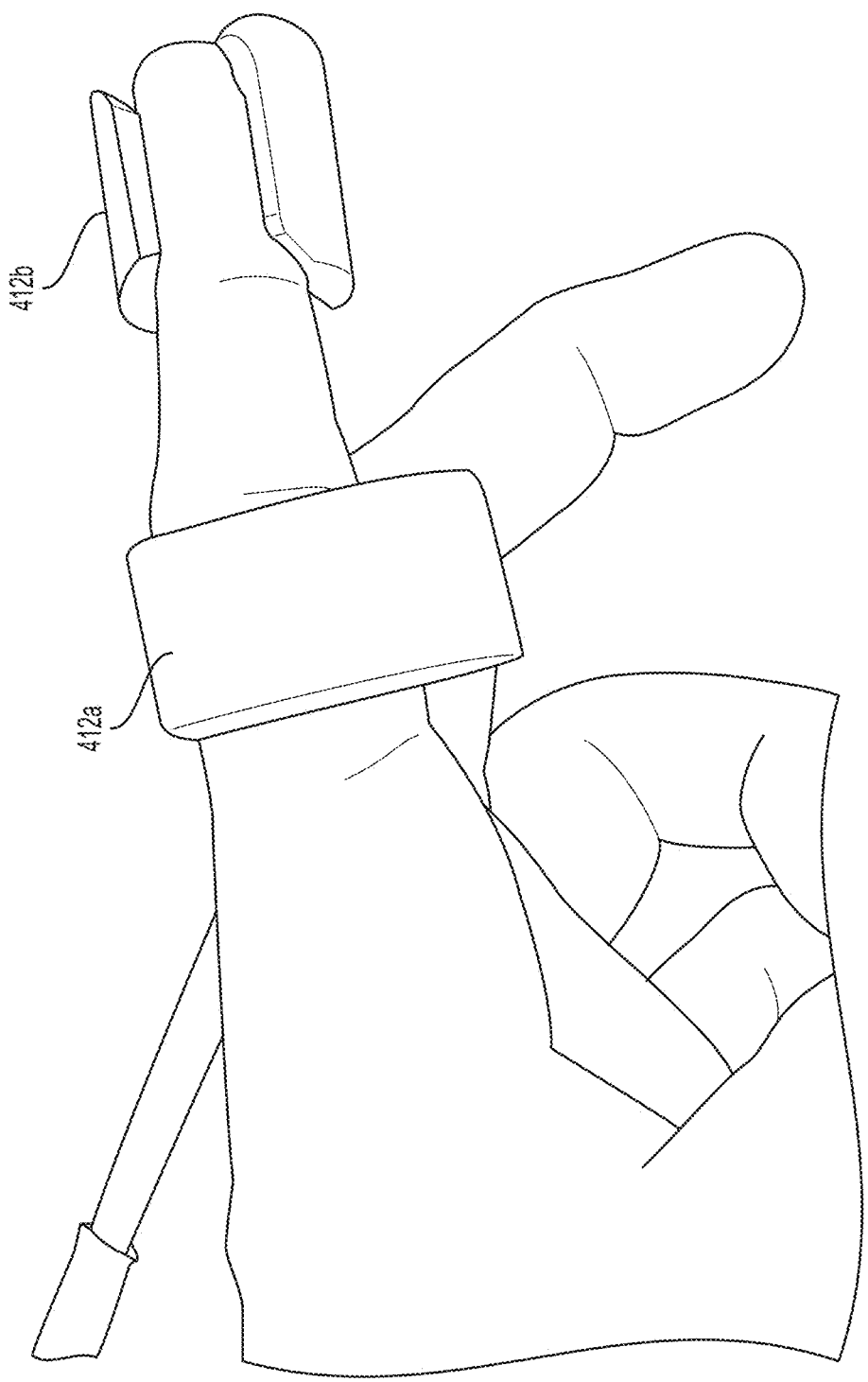
Figure 4K:
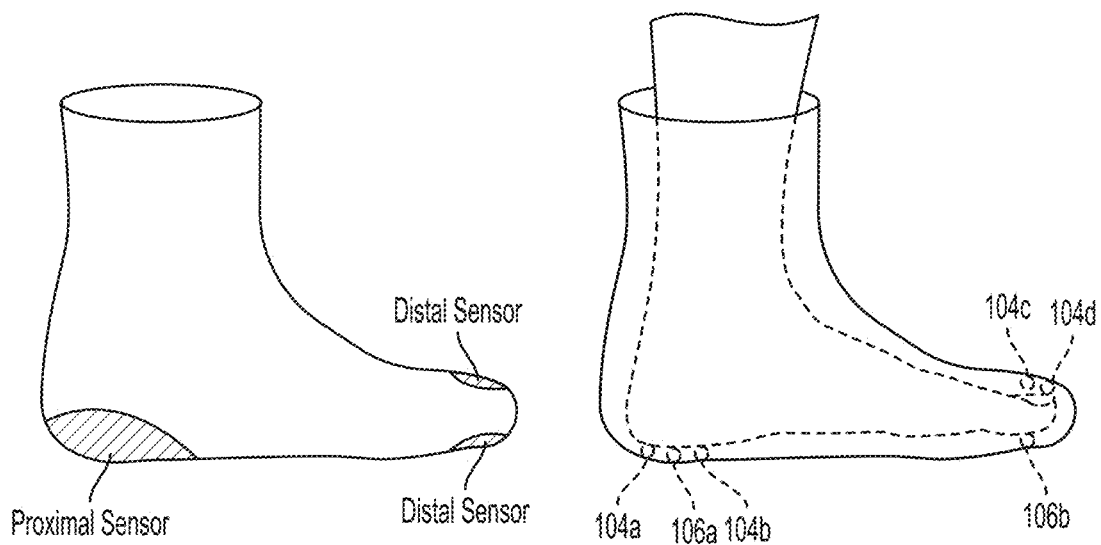
FIGS. 4K-4L illustrate exemplary embodiments of support structures designed to register with specific portions of human anatomy according to an embodiment of the invention.
Figure 4L:
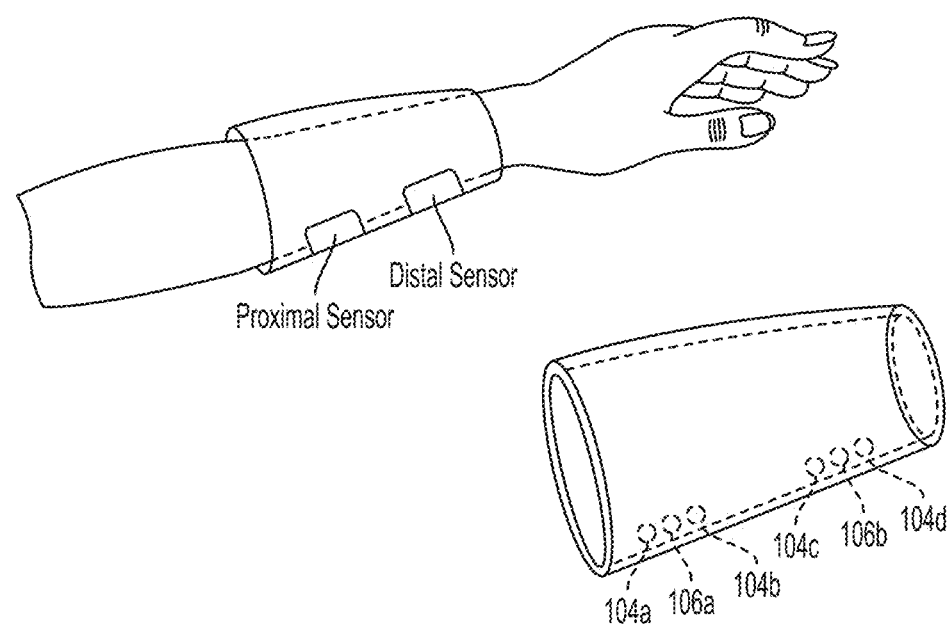

Referring now to FIGS. 4A-4G, a first pair of light sources 404a, 404b (e.g., blue light source 404a and green light source 404b) and a first photodetector 406a is located within a first unit 412a at the base (e.g., over a proximal phalanx) of a finger while a second pair of light sources 404c, 404d (e.g., red light source 404c and infrared light source 404d) and a second photodetector 406b is located within a second unit 412b positioned over a tip of the same finger. As further described in U.S. Provisional Patent Application Ser. No. 62/417,231, filed Nov. 3, 2016, and U.S. Provisional Patent Application Ser. No. 62/432,131, filed Dec. 9, 2016, distribution of light sources 404a, 404b, 404c, 404d and photodetectors 406a, 406b along a limb (e.g., a finger) facilitates measurement of blood pressure using pulse transit time. (An additional optional pulse oximetry sensor 414 is also depicted in FIGS. 4A and 4B, but is not essential to the invention described herein.)

Working Example 2

Figure 5:
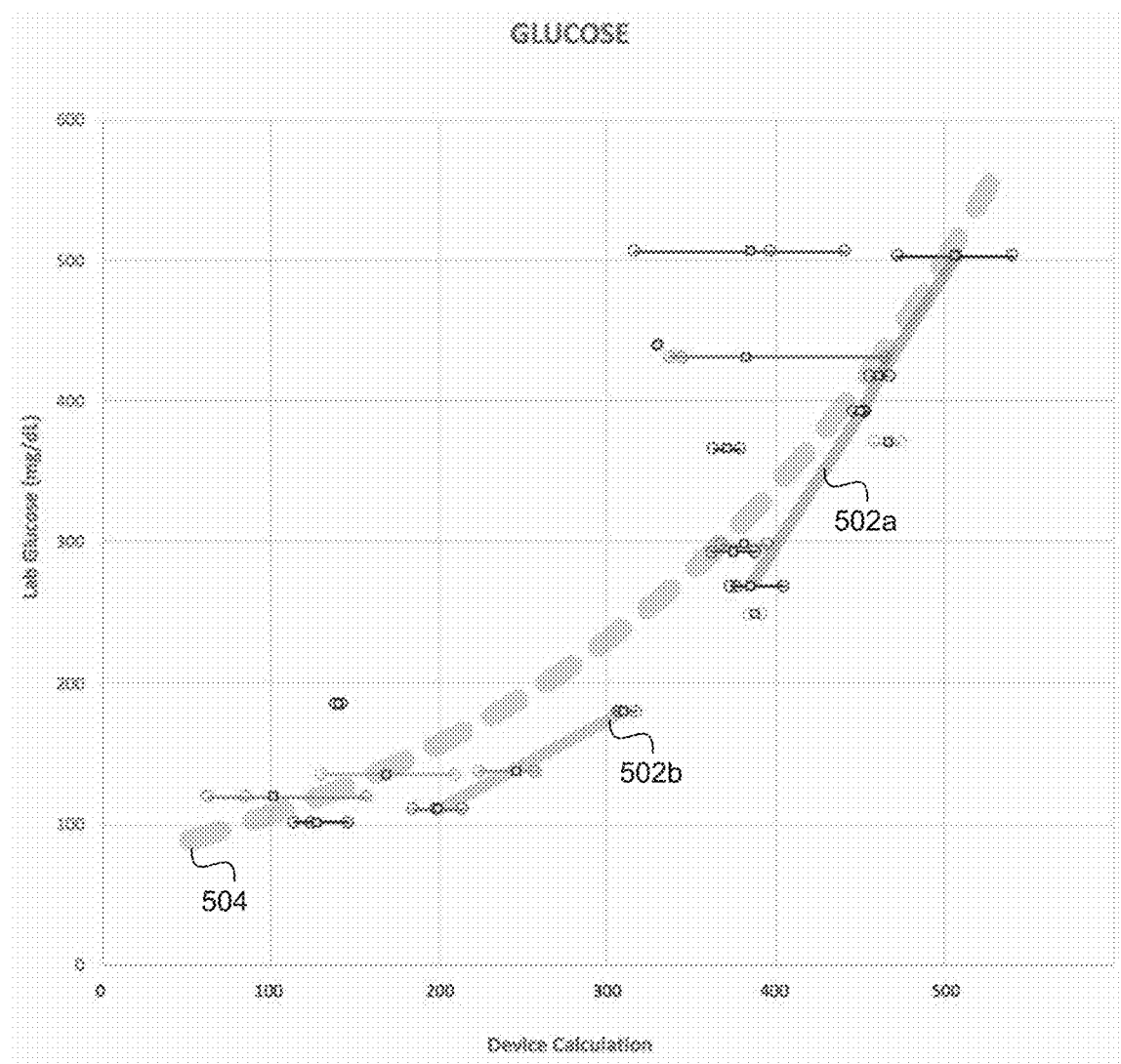
FIG. 5 plots the relationship of the raw device results (i.e., the Glucose Factor) to lab-measured glucose levels. The example calibration equation is shown in as the thick dashed line.

FIG. 5 plots the relationship of the raw device results (i.e., the Glucose Factor) to lab-measured glucose levels. The example calibration equation is shown in as the thick dashed line. The thick solid lines on the plot trace repeated tests on specific individuals. For example, the thick line 502a traces an individual as their glucose was treated with an insulin IV infusion. An example calibration curve is shown as the thick dashed line 504.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference.

APPENDIX

TABLE 6

Exemplary Components

| Component | Source | Product No. |
|---|---|---|
| Blue LED | Kingbright | APT1608LVBC/D |
| Green LED | Kingbright | APT1608LZGCK |

TABLE 6-continued

Exemplary Components

| Component | Source | Product No. |
|---|---|---|
| Red LED | Lite-On Electronics, Inc. | LTST-C171CKT |
| Infrared LED | SunLED | XZTNI54W |

The invention claimed is:

1. A non-invasive blood glucose meter comprising:
a sensor body configured to mate with a tissue surface;
a green light source;
one or more red light sources;
one or more infrared light sources;
a photodetector disposed on the sensor body at a suitable position for capturing light emanating from the tissue surface after emission from the one or more light sources; and
a controller programmed to:
receive one or more signals from the photodetector; and
calculate blood glucose value as function of at least the signals received from the photodetector after emission by at least one of the light sources;
wherein the controller is further programmed to calculate the blood glucose value based on a function of at least one of the terms $$\frac{R+G}{G}, \frac{IR+G}{G}, \text{ and } \frac{R+IR+G}{G},$$

wherein:
G is a measure of amplitude of the green light;
R is a measure of amplitude of the red light; and
IR is a measure of amplitude of the infrared light.

2. A non-invasive blood glucose meter comprising:
a sensor body configured to mate with a tissue surface;
a green light source;
a blue light source;
a red light source;
an infrared light source;
a photodetector disposed on the sensor body at a suitable position for capturing light emanating from the tissue surface after emission from the one or more light sources; and
a controller programmed to:
receive one or more signals from the photodetector; and
calculate blood glucose value as function of at least the signals received from the photodetector after emission by at least one of the light sources;
wherein the controller is further programmed to calculate the blood glucose value based on a function of at least one of the terms $$\frac{R+B+G}{B}, \frac{IR+B+G}{B}, \text{ and } \frac{R+IR+B+G}{B},$$

wherein:
B is a measure of amplitude of detected blue light;
G is a measure of amplitude of detected green light;
R is a measure of amplitude of detected red light; and
IR is a measure of amplitude of detected infrared light.

3. The non-invasive blood glucose meter of claim 2, wherein the controller is further programmed to calculate the blood glucose value using the equation $$\text{glucose} = (\alpha)\left(\frac{B}{G}\right) + (\beta)\left(\frac{B+G+R+IR}{B}\right) + (\gamma)\left(\frac{B+G+R+IR}{G}\right) + \frac{(\delta)^{\frac{B}{G}}}{(\varepsilon)} + (\zeta),$$

wherein α, β, γ, δ, ε, and ζ are calibration constants.

4. The non-invasive blood glucose meter of claim 3, wherein:
α is about 150;
β is about 0.5;
γ is about 0.5;
δ is about 3.0;
ε is about 2.0; and
ζ is about −25.

5. The non-invasive blood glucose meter of claim 2, wherein the controller is further programmed to calculate the blood glucose value using an expression of $\mu e^{\nu(\textit{Glucose Factor})}$, wherein μ and ν are calibration constants.

6. The non-invasive blood glucose meter of claim 5, wherein in the $\mu e^{\nu(\textit{Glucose Factor})}$:
μ is about 53.961; and
ν is about 0.4006.

7. The non-invasive blood glucose meter of claim 5, wherein $$\text{Glucose Factor} = \frac{\alpha - B\ln\frac{B}{\beta} - G\ln\frac{B}{\gamma} - \varepsilon\ln\frac{B}{\delta} - B\ln\frac{G}{\zeta} - G\ln\frac{G}{\eta} - \iota\ln\frac{G}{\theta} + \kappa\frac{B+G+R+IR}{B+G}}{\lambda},$$

wherein α, β, γ, δ, ε, ζ, η, θ, ι, κ, and λ are calibration constants.

8. The non-invasive blood glucose meter of claim 7, wherein:
α is about 100,000;
β is about 1,500;
γ is about 1,500;
δ is about 1,500;
ε is about 3,000;
ζ is about 2,500;
η is about 2,500;
θ is about 2,500;
ι is about 5,000;
κ is about 200; and
λ is about 25,000.

9. A method of non-invasively determining a blood glucose level, the method comprising:
receiving one or more absorption measurements of two or more wavelengths, wherein at least one of the two or more wavelengths includes one or more wavelengths selected from the group consisting of: blue light and green light; and
calculating a blood glucose value based on a function of at least one of the terms selected from the group consisting of $$\frac{R+B}{B}, \frac{IR+B}{B}, \frac{R+IR+B}{B}, \frac{R+G}{G}, \frac{IR+G}{G}, \frac{R+IR+G}{G},$$

-continued $$\frac{R+B+G}{B}, \frac{IR+B+G}{B}, \frac{R+IR+B+G}{B}, \frac{R+B+G}{G},$$

$$\frac{IR+B+G}{G}, \text{ and } \frac{R+IR+B+G}{G}$$

wherein:
B is a measure of amplitude of the blue light;
G is a measure of amplitude of the green light;
R is a measure of amplitude of red light in one or more absorption measurements; and
IR is a measure of amplitude of infrared light in one or more absorption measurements.

10. The method of claim 9, wherein the function includes $$\text{glucose} = (\alpha)\left(\frac{B}{G}\right) + (\beta)\left(\frac{B+G+R+IR}{B}\right) + (\gamma)\left(\frac{B+G+R+IR}{G}\right) + \frac{(\delta)^{\frac{B}{G}}}{(\varepsilon)} + (\zeta),$$

wherein $\alpha$, $\beta$, $\gamma$, $\delta$, $\varepsilon$, and $\zeta$ are calibration constants.

11. The method of claim 9, wherein the controller is further programmed to calculate the blood glucose value using an expression of $\mu e^{\nu(Glucose\ Factor)}$, wherein $\mu$ and $\nu$ are calibration constants.

12. The method of claim 11, wherein in the expression $\mu e^{\nu(Glucose\ Factor)}$:
$\mu$ is about 53.961; and
$\nu$ is about 0.4006.

13. The method of claim 11, wherein $$\text{Glucose Factor} = \frac{\alpha - B\ln\frac{B}{\beta} - G\ln\frac{B}{\gamma} - \varepsilon\ln\frac{B}{\delta} - B\ln\frac{G}{\zeta} - G\ln\frac{G}{\eta} - \iota\ln\frac{G}{\theta} + \kappa\frac{B+G+R+IR}{B+G}}{\lambda},$$

wherein $\alpha$, $\beta$, $\gamma$, $\delta$, $\varepsilon$, $\zeta$, $\eta$, $\theta$, $\iota$, $\kappa$, and $\lambda$ are calibration constants.

14. A non-invasive blood glucose sensor comprising:
a sensor body configured to mate with a tissue surface;
a plurality of light sources configured to emit light to the tissue surface, the plurality of light sources comprising:
  a first blue light source disposed on the sensor body;
  a second blue light source disposed on the sensor body;
  a first green light source disposed on the sensor body;
  a second green light source disposed on the sensor body;
  a first red light source disposed on the sensor body;
  a second red light source disposed on the sensor body;
  an first infrared light source disposed on the sensor body; and
  a second infrared light source disposed on the sensor body;
a photodetector disposed on the sensor body at a position for capturing light emanating from the tissue surface after emission from the plurality of light sources; and
a controller programmed to:
  receive one or more signals from the photodetector; and
  calculate blood glucose value as function of at least the one or more signals received from the photodetector after emission by the plurality of light sources,
wherein the controller is further programmed to calculate the blood glucose value based on a function of at least one of:
  a measure of detected amplitude of the first blue light;
  a measure of detected amplitude of the second blue light;
  a measure of detected amplitude of the first green light;
  a measure of detected amplitude of the second green light;
  a measure of detected amplitude of the first red light;
  a measure of detected amplitude of the second red light;
  a measure of detected amplitude of the first infrared light; and
  a measure of detected amplitude of the second infrared light;
wherein the controller is further programmed to calculate the blood glucose value using an expression of $\mu e^{\nu(Glucose\ Factor)}$, wherein $\mu$ and $\nu$ are calibration constants.

* * * * *